(12) United States Patent
Jiao

(10) Patent No.: US 9,839,605 B2
(45) Date of Patent: Dec. 12, 2017

(54) BOROJO SKIN CARE PRODUCT AND USE THEREOF FOR NATURAL MOISTURIZING, ANTI-AGEING, ANTI-UV, ANTI-ANAPHYLAXIS AND WHITENING

(71) Applicants: GUANGZHOU YIJIAN BIOMEDICAL TECHNOLOGY DEVELOPMENT CO. LTD, Guangzhou (CN); Hong Jiao, Guangzhou (CN)

(72) Inventor: Hong Jiao, Guangzhou (CN)

( * ) Notice: Subject to any disclaimer, the term of this patent is extended or adjusted under 35 U.S.C. 154(b) by 0 days.

(21) Appl. No.: 15/164,864

(22) Filed: May 25, 2016

(65) Prior Publication Data

US 2016/0346194 A1    Dec. 1, 2016

Related U.S. Application Data

(63) Continuation of application No. PCT/CN2014/087111, filed on Sep. 22, 2014.

(30) Foreign Application Priority Data

Mar. 13, 2013  (CN) .......................... 2014 1 0093671

(51) Int. Cl.
| | | |
|---|---|---|
| A61K 8/9789 | (2017.01) |
| A61Q 19/00 | (2006.01) |
| A61Q 19/02 | (2006.01) |
| A61Q 19/08 | (2006.01) |
| A61K 8/97 | (2017.01) |
| A61K 8/37 | (2006.01) |
| A61K 8/58 | (2006.01) |
| A61Q 17/04 | (2006.01) |

(52) U.S. Cl.
CPC ............ *A61K 8/97* (2013.01); *A61K 8/375* (2013.01); *A61K 8/585* (2013.01); *A61K 8/9789* (2017.08); *A61Q 17/04* (2013.01); *A61Q 19/00* (2013.01); *A61Q 19/004* (2013.01); *A61Q 19/02* (2013.01); *A61Q 19/08* (2013.01); *A61K 2800/782* (2013.01); *A61K 2800/85* (2013.01)

(58) Field of Classification Search
CPC .............. A61K 8/9789; A61K 2800/85; A61Q 19/004; A61Q 19/02; A61Q 19/08
See application file for complete search history.

(56) References Cited

U.S. PATENT DOCUMENTS

| | | | |
|---|---|---|---|
| 8,142,823 B2 * | 3/2012 | Shatkina ............ | A61K 8/0212 424/725 |
| 2009/0246231 A1 * | 10/2009 | Valencia ................. | A61K 8/97 424/400 |

FOREIGN PATENT DOCUMENTS

WO   WO 2011104448 A2 *  9/2011  .......... A61K 8/0216

OTHER PUBLICATIONS

Zhang Yanchao, Li Hong, Ming Hongyan, Chen Chen, Gao Chengbiao, Shi Yonggang, Du Zhenjia, Chen Zuozuo and Jiao Hong, "Detect the Fatty Acid in Borojo Powder by Gas Chromatography-Mass Spectrometry", Food Research and Development, 2014, 2, 73-76.*

Li, Hong, et al. "The Protection Effects Against Ultraviolet A Radiation Damages in NIH-3T3 Cells of Borojo Fruit Powder and Extracts [J]." Chinese Journal of Aesthetic Medicine 18 (2012): 055.*

* cited by examiner

*Primary Examiner* — John Pak
*Assistant Examiner* — Nathan W Schlientz
(74) *Attorney, Agent, or Firm* — Wayne & Ken, LLC; Tony Hom

(57) ABSTRACT

A Borojo skin care product and a preparation method thereof are disclosed. The skin care product comprises a matrix and Borojo powder, and the preparation method thereof comprises the steps: mixing and homogeneously stirring the Borojo powder in the matrix to obtain the Borojo skin care product.

3 Claims, 13 Drawing Sheets

BOROJO SKIN CARE PRODUCT AND USE THEREOF FOR NATURAL MOISTURIZING, ANTI-AGEING, ANTI-UV, ANTI-ANAPHYLAXIS AND WHITENING

CROSS-REFERENCE TO RELATED APPLICATIONS

This application is a continuation of International Patent Application No. PCT/CN2014/087111 with an international filing date of Sep. 22, 2014 designating the United States, now pending and further claims priority benefits to Chinese Patent Application No. 201410093671.7 filed Mar. 13, 2014. The content of the aforementioned applications, including any intervening amendments thereto, is incorporated herein by reference.

TECHNICAL FIELD

The present invention relates to the field of skin care products, in particular to a skin care product with the effects of natural moisturizing, anti-ageing, anti-UV, anti-anaphylaxis and whitening.

BACKGROUND

Borojo is a fruit growing in the tropical rainforest of South America, and is the only *Borojoa cuatrec* genus of Rubiaceae adaptive to the climates in Ecuador. Borojo fruits have a diameter of 7-12 cm, are green before ripening, become dark brown after ripening, and each weigh 700-1000 g; the flesh is soft, is sour and viscous in taste, and accounts for 88% by weight after deseeding. Fresh Borojo is a fruit having high sourness (pH 2.74), low moisture (69.22%), high carbohydrate (28.02%), low sugar (9.72%), high protein (1.22%) and high dietary fiber (2.98%). The contents of B1 and B2 of vitamin B, niacin, folic acid and vitamin E are much higher than most of fruits. The total content of free amino acids is 1.35%, including 25 free amino acids; after hydrolysis, it contains 19 amino acid substances, up to 2.51%, including 5 amino acids essential to a human body and 2 conditionally essential amino acids. Borojo is rich in trace elements, containing potassium 3500 of mg/kg, magnesium of 280 mg/kg, iron of 160 mg/kg and zinc of 0.64 mg/kg; and Borojo contains trace elements essential to the human body, such as zinc, copper, cobalt and iron, possibly essential trace elements such as manganese, silicon, nickel and boron, as well as trivalent chromium and nickel rare in fruits and vegetables. The total amount of rare earth and the content of 16 rare earth elements are within normal limits, thereby having no potential hazard to the human health. The content of harmful heavy metal lead is 24 μg/kg; and the contents of mercury, arsenic and cadmium are below a minimal detection limit. Borojo is rich in linoleic acid (9.91%) and linolenic acid (0.89%) essential to the human body, and has total flavonoids up to 335.2 mg/kg, 8, 9-iridoid glycoside up to 1.92 g/100 g, and polyphenol up to 270 mg/kg.

Borojo is a fruit with high nutritional value, but the application of Borojo in the field of skin care products is not scientifically reported currently.

SUMMARY

The present invention aims to overcome the shortcomings of the prior art and provide a skin care product containing Borojo powder, wherein the skin care product has the effects of natural moisturizing, anti-ageing, anti-UV, anti-anaphylaxis and whitening.

To achieve the above objectives, the present invention adopts a technical solution that a Borojo skin care product contains a matrix, and the skin care product also contains the Borojo powder.

The matrix described in the present invention is a basic ingredient of cosmetics, and can be chosen reasonably by those skilled in the art based on the prior art, wherein the matrix can be prepared from different ingredients, to obtain the matrixes of different kinds of skin care products. Different matrixes can be combined with the contained Borojo powder to obtain the skin care products with the different effects of moisturizing, anti-ageing, sun-protecting, anti-anaphylaxis and whitening Borojo, namely, the Borojo powder can perform the functions of moisturizing, anti-ageing, anti-UV, anti-anaphylaxis and whitening in combination with different matrix ingredients in the prior art.

As a preferred embodiment of the Borojo skin care product of the present invention, the Borojo powder is prepared by a met hod comprising the following steps:

(1) taking fresh Borojo fruits, cleaning and peeling, and separating kernels from the fruits;

(2) adding water of 10% by weight of fruit flesh to the fruit flesh, grinding, then adding pectinase of 1% by weight of fruit flesh, conducting enzymatic digestion on the fruit flesh for 1.5 hours at 30-40° C.;

(3) pressing and filtering the fruit flesh after enzymatic digestion and removing impurities, heating to 80° C. and keeping the temperature for 5 min, and killing the enzyme;

(4) adding sodium carbonate of 5% by weight of fruit flesh to adjust the pH, and then concentrating in vacuum at −65° C. until the BRIX reaches 20%; and (5) adding beta-cyclodextrin of 1% by weight of the fruit flesh, and then spraying-drying to obtain the Borojo powder.

The BRIX in the step (4) means the content of soluble solids in the product. The Borojo powder in the skin care product is prepared by using the specific method mentioned above, and the obtained Borojo powder has better effects of anti-ageing, anti-UV, anti-anaphylaxis and whitening.

The nutritional ingredients of the Borojo powder prepared by the method mentioned above are shown in the table below:

| Item | Unit | Content range | Average value |
| --- | --- | --- | --- |
| Calories | kcal/100 g | 351.2-343.9 | 348.1 |
| Carbohydrate | % | 84.4-81.7 | 83.2 |
| Dietary fiber | % | 4.05-5.50 | 4.70 |
| Moisture | % | 4.25-4.86 | 4.52 |
| Protein | % | 1.30-1.43 | 1.38 |
| Fat | % | 0.038-0.045 | 0.042 |
| Phosphate | mg/kg | 1330-1496 | 1314.3 |
| Total sugar | % | 35.4-37.8 | 36.7 |
| Total acid | % | 1.40-1.41 | 1.41 |
| PH value | | 4.04-4.09 | 4.07 |
| Ash | % | 6.0-6.5 | 6.2 |
| Acid-insoluble ash | % | 0.44-0.48 | 0.46 |
| VitB2 | mg/kg | 2.10-2.47 | 2.28 |
| VitB3 (niacin) | mg/kg | 4.98-6.13 | 5.47 |
| VitB5 (pantothenic acid) | mg/kg | 37.1-44.8 | 41.3 |
| VitE | mg/kg | 0.899-0.939 | 0.916 |
| Total free amino acid after hydrolysis | % | 1.19-1.29 | 1.24 |
| Potassium | mg/kg | 15724.5-15956.44 | 15820.22 |
| Sodium | mg/kg | 10783.05~14195.64 | 11938.54 |
| Calcium | mg/kg | 496.79-526.10 | 509.60 |
| Magnesium | mg/kg | 983.13-985.17 | 984.46 |

-continued

| Item | Unit | Content range | Average value |
|---|---|---|---|
| Iron | mg/kg | 17.91-18.07 | 17.97 |
| Copper | mg/kg | 1.2-1.3 | 1.3 |
| Zinc | mg/kg | 2.5-2.7 | 2.6 |
| Chromium | mg/kg | 5.33-5.76 | 5.49 |
| Lauric acid | % | 1.47-1.58 | 1.52 |
| Palmitic acid | % | 18.59-20.22 | 19.58 |
| Oleic acid | % | 7.182-7.73 | 7.52 |
| Stearic acid | % | 12.97-14.05 | 13.69 |
| Arachidic acid | % | 1.77-1.86 | 1.80 |
| Erucic acid | % | 0.93-1.12 | 1.01 |
| Linoleic acid | % | 47.96-64.01 | 54.88 |
| Polyphenol | mg/100 g | 270.0-273.6 | 270.4 |
| Total flavonoids | mg/kg | 189.9-460.1 | 334.2 |
| 8,9-iridoid glycoside | g/100 g | 1.90-1.94 | 1.92 |

As the preferred embodiment of the Borojo skin care product of the present invention, the mass concentration of the Borojo powder in the skin care product is 0.1%-5%. The mass concentration of the Borojo powder in the skin care product is preferably 5%, because the whitening effect of the Borojo skin care product obtained at this concentration is particularly significant.

As the preferred embodiment of the Borojo skin care product of the present invention, the matrix comprises the following components in parts by weight: 50-70 parts of water, 2-10 parts of glycerol, 2-10 parts of caprylic/capric triglyceride, 1-7 parts of titanium dioxide, 1-7 parts of squalane, 0.1-3 parts of C30-45 alkyl dimethicone or polycyclohexene oxide cross-linked polymer, 0.1-3 parts of panthenol, 0.1-3 parts of decamethylcyclopentasiloxane, 0.1-3 parts of cetearyl alcohol, 0.1-3 parts of C12-20-alkyl glucoside, 0.1-3 parts of sodium acrylates copolymer or mineral oil or PPG-1 trideceth-6, 0.1-3 parts of polydimethylsiloxane, 0.1-3 parts of PEG-20 methyl glucose sesquistearate, an appropriate amount of methylisothiazolinone, an appropriate amount of ethylhexylglycerin, 0.01-1 part of carbomer, 0.01-1 part of xanthan gum, 0.01-1 part of triethanolamine, and 0.01-0.2 part of disodium EDTA. When the matrix contains the components described above, the Borojo skin care product formed by the matrix and the Borojo powder mainly has the effect of anti-ageing. The matrix is prepared by a method comprising the following steps:

(1) weighing raw materials of an oil phase: cyclic dimethylpolysiloxane, caprylic/capric triglyceride, titanium dioxide, squalane, decamethylcyclopentasiloxane, cetyl stearyl alcohol, C12-20 alkyl glucoside, polydimethylsiloxane, PEG-20 methyl glucose sesquistearate, and C30-45 alkyl dimethicone or polycyclohexene oxide cross-linked polymer; and feeding the raw materials into an emulsifying pot, heating and dissolving;

(2) weighing the raw materials of an aqueous phase: water, glycerin, panthenol, carbomer, xanthan gum and disodium EDTA; and feeding the raw materials into a water pot, stirring uniformly, heating and dissolving; and (3) opening the emulsifying pot for stirring, opening the vacuum for pumping in the aqueous phase, adding triethanolamine and sodium acrylates copolymer or mineral oil or PPG-1 trideceth-6, stirring homogeneously, then cooling down, feeding the weighed methylisothiazolinone and ethylhexylglycerin, stirring uniformly, discharging the obtained material, to obtain the matrix of the skin care product for anti-ageing.

As the preferred embodiment of the Borojo skin care product of the present invention, the matrix comprises the following components in parts by weight: 60-80 parts of water, 3-10 parts of cyclic dimethylpolysiloxane, 3-10 parts of C12-15 alkyl benzoate, 3-10 parts of isopropyl myristate, 3-10 parts of propylene glycol, 2-10 parts of glycerin, 1-5 parts of cetearyl alcohol, 1-5 parts of polydimethylsiloxane, 0.5-5 parts of PEG-100 stearate, 0.1-5 parts of PEG-20 methyl glucose sesquistearate, 0.1-5 parts of glycerol stearate, 0.1-5 parts of methyl glucose sesquistearate, 01-5 parts of tocopherol acetate, 0.3-1 part of polyacrylamide and C13-14 isoparaffin and laureth-7, 0.1-1 part of C12-13 potassium alcohol phosphate, 0.1-1 part of vitamin P or hexadecene copolymer, 0.1-1 part of potassium azelaoyl diglycinate, 01-1 part of bis(hydroxymethyl) imidazolidinyl urea and iodopropynyl butylcarbamate, 0.1-1 part of alpha-bisabolol, 0.1-1 part of allantoin, 0.05-0.2 part of methylparaben, 0.1-0.5 part of xanthan gum, 0.05-0.2 part of propylparaben, 0.02-1 part of menthyl lactate, and 0.02-1 part of sweet orange flower oil. When the matrix contains the components described above, the Borojo skin care product formed by the matrix and the Borojo powder mainly has the effects of anti-UV and sun-protecting. The matrix is prepared by a method comprising the following steps:

(1) weighing raw materials of an oil phase: cyclic dimethylpolysiloxane, C12-15 alcohol benzoate, isopropyl myristate, cetearyl alcohol, polydimethylsiloxane, PEG-100 stearate, PEG-20 methyl glucose sesquistearate, glyceryl stearate, methyl glucose sesquistearate, tocopherol acetate, alpha-bisabolol, methylparaben and propylparaben; and feeding the raw materials into an emulsifying pot, heating to dissolve;

(2) weighing the raw materials of an aqueous phase: water, propylene glycol, glycerin, xanthan gum, allantoin, C12-13 potassium alcohol phosphate, vitamin P or hexadecene copolymer; feeding the raw materials into a water pot, stirring uniformly; and (3) opening the emulsifying pot for stirring, pumping in the aqueous phase, adding polyacrylamide or C13-14 isoparaffin or laureth-7 and allantoin, performing homogenization for three minutes, cooling down; adding potassium azelaoyl diglycinate, menthyl lactate, sweet orange flower oil, and bis(hydroxymethyl) imidazolidinyl urea or iodopropynyl butylcarbamate; stirring the raw materials uniformly, discharging the obtained material, to obtain the matrix of the skin care product for anti-UV and sun-protecting.

As the preferred embodiment of the Borojo skin care product of the present invention, the matrix comprises the following components in parts by weight: 75-90 parts of water, 1-10 parts of butanediol, 1-10 parts of glycerin, 1-5 parts of beta-glucan, an appropriate amount of phenoxyethanol, 0.05-0.5 part of hydroxyethyl cellulose, 0.05-0.5 part of allantoin, 0.05-0.5 part of disodium EDTA, an appropriate amount of methylparaben, an appropriate amount of PEG-60 hydrogenated castor oil, and an appropriate amount of essence. When the matrix contains the components described above, the Borojo skin care product formed by the matrix and the Borojo powder mainly has the effect of anti-anaphylaxis. The matrix is prepared by a method comprising the following steps:

(1) weighing the raw materials of an aqueous phase: water, butanediol, glycerin, hydroxyethyl cellulose, allantoin, disodium EDTA, methylparaben; and feeding the raw materials into a stirring pot, cooling after heating and dissolving; and (2) adding the weighed beta-glucan, phenoxyethanol, PEG-60 hydrogenated castor oil and essence; stirring uniformly, discharging the obtained material, to obtain the matrix of the skin care product for anti-anaphylaxis.

As the preferred embodiment of the Borojo skin care product of the present invention, the matrix comprises the following components in parts by weight: 50-70 parts of water, 1-10 parts of glycerin, 1-10 parts of hydrogenated polydecene, 1-10 parts of ethylhexyl palmitate, 1-10 parts of butanediol, 1-10 parts of cyclic polydimethylsiloxane, 0.1-5 parts of cetearyl alcohol, 0.1-5 parts of C12-20 alkyl glucoside, 0.1-5 parts of C13-14 isoparaffin, 0.1-5 parts of PEG-100 stearate, 0.1-5 parts of polyacrylamide, 0.1-5 parts of polydimethylsiloxane, 0.1-5 parts of laureth-7, 0.1-5 parts of titanium dioxide, 0.1-5 parts of tocopherol acetate, 0.1-1 part of allantoin, 0.1-1 part of xanthan gum, 0.1-1 part of tranexamic acid, an appropriate amount of essence, 0.1-1 part of sodium hyaluronate, 0.1-1 part of phenoxyethanol.

When the matrix contains the components described above, the Borojo skin care product formed by the matrix and the Borojo powder mainly has the effect of whitening. The matrix is prepared by a method comprising the following steps:

(1) weighing raw materials of an oil phase: hydrogenated polydecene, ethylhexyl palmitate, cyclic polydimethylsiloxane, cetearyl alcohol, C12-20 alkyl glucoside, PEG-100 stearate, polydimethylsiloxane and tocopheryl acetate; feeding the raw materials into an emulsifying pot, heating and dissolving;

(2) weighing the raw materials of an aqueous phase: water, glycerin, butanediol, allantoin, xanthan gum, sodium hyaluronate and titanium dioxide; feeding the raw materials to a water pot, heating and stirring uniformly;

(3) opening the emulsifying pot for stirring, pumping in the aqueous phase, adding C13-14 isoparaffin, polyacrylamide and laureth-7, homogenizing for three minutes, cooling down, feeding the weighed tranexamic acid, essence and phenoxyethanol, stirring uniformly, and discharging the obtained material, to obtain the matrix of the skin care product for whitening.

In the matrixes of the skin care products for various effects, the appropriate amount in the components can be known well by those skilled in the art according to the requirements and the prior art.

The present invention also provides a preparation method of the Borojo skin care product, wherein the method comprises the steps of mixing and uniformly stirring the Borojo powder in the matrix to obtain the product. The Borojo skin care product of the present invention can be obtained by simply mixing and uniformly dispersing the Borojo powder in the matrix, wherein the matrixes may be different kinds of matrixes of the skin care products for different effects in the prior art; different matrixes can be mixed with the Borojo powder of the present invention to obtain the Borojo skin care products with different effects, mainly including the effects of moisturizing, anti-ageing, anti-UV, anti-anaphylaxis and whitening.

Further, the present invention also provides a use of the Borojo powder in the skin care product, wherein the Borojo powder is prepared by a method comprising the following steps:

(1) taking fresh Borojo fruits, cleaning and peeling, and separating kernels from the fruits;

(2) adding water of 10% by weight of fruit flesh to the fruit flesh, grinding, then adding pectinase of 1% by weight of fruit flesh, conducting enzymatic digestion on the fruit flesh for 1.5 hours at 30-40° C.;

(3) pressing and filtering the fruit flesh after enzymatic digestion and removing impurities, heating to 80° C. and keeping the temperature for 5 min, and killing the enzyme;

(4) adding sodium carbonate of 5% by weight of fruit flesh to adjust the pH, and then concentrating in vacuum at −65° C. until the BRIX reaches 20%; and (5) adding beta-cyclodextrin of 1% by weight of the fruit flesh, and then spraying-drying to obtain the Borojo powder. The Borojo powder of the present invention has the effects of moisturizing, anti-ageing, anti-UV, anti-anaphylaxis and whitening, and can be used in combination with various skin care product matrixes to obtain the Borojo skin care products with the effects of moisturizing, anti-ageing, anti-UV, anti-anaphylaxis and whitening.

As the preferred embodiment of the use of the Borojo powder of the present invention in the skin care products, the mass concentration of the Borojo powder in the skin care product is 0.1%-5%. When the mass concentration of the Borojo powder in the skin care product is 0.1%-5%, the Borojo can be better to develop the effects of moisturizing, anti-ageing, anti-UV, anti-anaphylaxis and whitening in the skin care products.

The specific Borojo powder is added to the Borojo skin care products of the present invention, and can be combined with different matrixes to obtain the Borojo skin care products with the effects of anti-ageing, anti-UV, anti-anaphylaxis and whitening. The preparation methods of the Borojo skin care products of the present invention are simple to operate, and can conveniently and rapidly prepare the Borojo skin care products with the effects of anti-ageing, anti-UV, anti-anaphylaxis and whitening. The use of the Borojo powder of the present invention is found by an inventor of the present application through a great deal of studies; the Borojo powder prepared by the method has the effects of anti-ageing, anti-UV, anti-anaphylaxis and whitening when the Borojo powder is used in the skin care products, and can be combined with different kinds of matrixes to obtain different kinds of skin care products with the effects of moisturizing, anti-ageing, anti-UV, anti-anaphylaxis and whitening.

DESCRIPTION OF THE DRAWINGS

FIG. 7A is the blank group. FIG. 7B is the matrix group, FIG. 7C is the Borojo group, FIG. 7D is the positive control group, FIG. 7E is the Borojo+positive control group.

DETAILED DESCRIPTION

Figure 1:
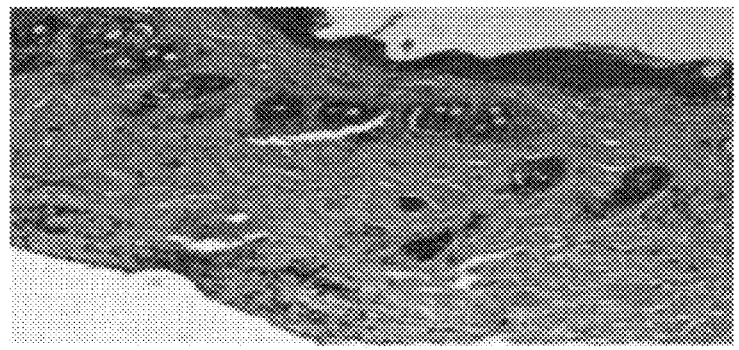
FIG. 1 is a pathological morphology of skin tissues of mice in a blank group.

To better explain the objectives, technical solutions and advantages of the present invention, the present invention is explained in detail below in combination with the drawings and specific embodiments.

Embodiment 1

In one embodiment of the Borojo skin care product of the present invention, the Borojo skin care product of the embodiment comprises the matrix and the Borojo powder, wherein the Borojo powder is prepared by using the preparation method of the summary part mentioned above; the mass concentration of the Borojo powder in the skin care product is 0.1%-5%; and the Borojo skin care product of the embodiment is prepared by the method comprising the following steps:

1. Preparation of the matrix 1.1 weighing the following raw materials of the oil phase in parts by weight: 2 parts of cyclic dimethylpolysiloxane, 10 parts of caprylic/capric triglyceride, 7 parts of titanium dioxide, 1 part of squalane, 0.1 part of decamethylcyclopentasiloxane, 3 parts of cetyl stearyl alcohol, 0.1 part of C12-20 alkyl glucoside, 0.1 part of polydimethylsiloxane, 3 parts of PEG-20 methyl glucose sesquistearate, and 0.1 part of C30-45 alkyl dimethicone or polycyclohexene oxide cross-linked polymer; and feeding the raw materials into the emulsifying pot, heating and dissolving;

1.2 weighing the following raw materials of the aqueous phase in parts by weight: 50 parts of water, 10 parts of glycerin, 3 parts of panthenol, 0.01 part of carbomer, 1 part of xanthan gum and 0.01 part of disodium EDTA; and feeding the raw materials into the water pot, stirring uniformly, heating and dissolving; and 1.3 opening the emulsifying pot for stirring, opening the vacuum for pumping in the aqueous phase, adding 1 part by weight of triethanolamine and 0.1 part by weight of sodium acrylates copolymer or mineral oil or PPG-1 trideceth-6, stirring homogeneously, then cooling down, feeding 0.2 part by weight of methylisothiazolinone and 0.5 part by weight of ethylhexylglycerin, stirring uniformly, discharging the obtained material, to obtain the matrix.

2. Preparation method of the Borojo skin care product: uniformly mixing and dispersing the Borojo powder in the matrix prepared in the step 1 to obtain a Borojo anti-ageing cream.

Embodiment 2

In one embodiment of the Borojo skin care product of the present invention, except the matrix, the remainder of the skin care product of the embodiment is same as the Embodiment 1. The matrix in the Borojo skin care product of the embodiment comprises the following components in parts by weight: 70 parts of water, 2 parts of glycerol, 2 parts of caprylic/capric triglyceride, 1 part of titanium dioxide, 7 parts of squalane, 3 parts of C30-45 alkyl dimethicone or polycyclohexene oxide cross-linked polymer, 0.1 part of panthenol, 3 parts of decamethylcyclopentasiloxane, 0.1 part of cetearyl alcohol, 3 parts of C12-20-alkyl glucoside, 3 parts of sodium acrylates copolymer or mineral oil or PPG-1 trideceth-6, 3 parts of polydimethylsiloxane, 0.1 part of PEG-20 methyl glucose sesquistearate, 1 part of methylisothiazolinone, 0.1 part of ethylhexylglycerin, 1 part of carbomer, 0.01 part of xanthan gum, 0.01 part of triethanolamine, and 0.2 part of disodium EDTA.

Embodiment 3

In one embodiment of the Borojo skin care product of the present invention, the Borojo skin care product of the embodiment comprises the matrix and the Borojo powder, wherein the Borojo powder is prepared by using the preparation method of the summary part mentioned above; the mass concentration of the Borojo powder in the skin care product is 0.1%-5%; and the Borojo skin care product of the embodiment is prepared by the method comprising the following steps:

1. Preparation of the matrix 1.1 weighing the following raw materials of the oil phase in parts by weight: 3 parts of cyclic dimethylpolysiloxane, 10 parts of C12-15 alcohol benzoate, 10 parts of isopropyl myristate, 5 parts of cetearyl alcohol, 5 parts of polydimethylsiloxane, 0.5 part of PEG-100 stearate, 0.1 part of PEG-20 methyl glucose sesquistearate, 5 parts of glyceryl stearate, 0.1 part of methyl glucose sesquistearate, 0.1 part of tocopherol acetate, 0.1 part of alpha-bisabolol, 0.05 part of methylparaben and 0.05 part of propylparaben; and feeding the raw materials into an emulsifying pot, heating to dissolve;

1.2 weighing the following raw materials of the aqueous phase in part by weight: 80 parts of water, 3 parts of propylene glycol, 2 parts of glycerin, 0.1 part of xanthan gum, 0.05 part of allantoin, 1 part of C12-13 potassium alcohol phosphate, and 1 part of vitamin P or hexadecene copolymer; feeding the raw materials into the water pot, stirring uniformly; and 1.3 opening the emulsifying pot for stirring, pumping in the aqueous phase, adding 1 part by weight of polyacrylamide or C13-14 isoparaffin or laureth-7 and 0.05 part by weight of allantoin, performing homogenization for three minutes, cooling down; adding 0.1 part by weight of potassium azelaoyl diglycinate, 1 part by weight of menthyl lactate, 0.02 part by weight of sweet orange flower oil, and 1 part by weight of bis(hydroxymethyl) imidazolidinyl urea or iodopropynyl butylcarbamate; stirring the raw materials uniformly, discharging the obtained material, to obtain the matrix.

2. Preparation of the Borojo skin care product: uniformly mixing and dispersing the Borojo powder in the matrix prepared in the step 1 to obtain a Borojo anti-UV repairing emulsion.

Embodiment 4

In one embodiment of the Borojo skin care product of the present invention, except the matrix, the remainder of the skin care product of the embodiment is same as the Embodiment 3. The matrix in the Borojo skin care product of the embodiment comprises the following components in parts by weight: 60 parts of water, 10 parts of cyclic dimethylpolysiloxane, 3 parts of C12-15 alkyl benzoate, 3 parts of isopropyl myristate, 0 part of propylene glycol, 10 parts of glycerin, 1 part of cetearyl alcohol, 1 part of polydimethylsiloxane, 5 parts of PEG-100 stearate, 5 parts of PEG-20 methyl glucose sesquistearate, 0.1 part of glycerol stearate, 5 parts of methyl glucose sesquistearate, 5 parts of tocopherol acetate, 0.3 part of polyacrylamide and C13-14 isoparaffin and laureth-7, 0.1 part of C12-13 potassium alcohol phosphate, 0.1 part of vitamin P or hexadecene copolymer, 1 part of potassium azelaoyl diglycinate, 0.1 part of bis (hydroxymethyl) imidazolidinyl urea and iodopropynyl butylcarbamate, 1 part of alpha-bisabolol, 1 part of allantoin, 0.2 part of methylparaben, 0.5 part of xanthan gum, 0.2 part of propylparaben, 0.02 part of menthyl lactate, and 1 part of sweet orange flower oil.

Embodiment 5

In one embodiment of the Borojo skin care product of the present invention, the Borojo skin care product of the embodiment comprises the matrix and the Borojo powder, wherein the Borojo powder is prepared by using the preparation method of the summary part mentioned above; the mass concentration of the Borojo powder in the skin care product is 0.1%-5%; and the Borojo skin care product of the embodiment is prepared by the method comprising the following steps:
1. Preparation of the matrix
1.1 weighing the following raw materials of the aqueous phase in parts by weight: 75 parts of water, 10 parts of butanediol, 10 parts of glycerin, 0.05 part of hydroxyethyl cellulose, 0.05 part of allantoin, 0.5 part of disodium EDTA, 1 part of methylparaben; and feeding the raw materials into the stirring pot, cooling after heating and dissolving; and
1.2 adding the weighed 1 part by weight of beta-glucan, 0.5 part by weight of phenoxyethanol, 0.2 part by weight of PEG-60 hydrogenated castor oil and 0.6 part by weight of essence; stirring uniformly, discharging the obtained material, to obtain the matrix.
2. Preparation of the Borojo skin care product: uniformly mixing and dispersing the Borojo powder in the matrix prepared in the step 1 to obtain a Borojo anti-anaphylaxis essence.

Embodiment 6

In one embodiment of the Borojo skin care product of the present invention, except the matrix, the remainder of the skin care product of the embodiment is same as the Embodiment 5. The matrix in the Borojo skin care product of the embodiment comprises the following components in parts by weight: 90 parts of water, 1 part of butanediol, 1 part of glycerin, 5 parts of beta-glucan, 1 part of phenoxyethanol, 0.5 part of hydroxyethyl cellulose, 0.5 part of allantoin, 0.05 part of disodium EDTA, 0.1 part of methylparaben, 1 part of PEG-60 hydrogenated castor oil, and 1 part of essence.

Embodiment 7

In one embodiment of the Borojo skin care product of the present invention, the Borojo skin care product of the embodiment comprises the matrix and the Borojo powder, wherein the Borojo powder is prepared by using the preparation method of the summary part mentioned above; the mass concentration of the Borojo powder in the skin care product is 01%5%; and the Borojo skin care product of the embodiment is prepared by the method comprising the following steps:
1. Preparation of the matrix
1.1 weighing the raw materials of the oil phase in parts by weight: 1 part of hydrogenated polydecene, 1 part of ethylhexyl palmitate, 10 parts of cyclic polydimethylsiloxane, 5 parts of cetearyl alcohol, 5 parts of C12-20 alkyl glucoside, 0.1 part of PEG-100 stearate, 0.1 part of polydimethylsiloxane and 0.1 part of tocopheryl acetate; feeding the raw materials into the emulsifying pot, heating and dissolving;
1.2 weighing the following raw materials of the aqueous phase in parts by weight: 70 parts of water, 1 part of glycerin, 10 parts of butanediol, 1 part of allantoin, 0.1 part of xanthan gum, 0.1 part of sodium hyaluronate and 5 parts of titanium dioxide; feeding the raw materials to the water pot, heating and stirring uniformly;
1.3 opening the emulsifying pot for stirring, pumping in the aqueous phase, adding 0.1 part by weight of C13-14 isoparaffin, 0.1 part by weight of polyacrylamide and 5 parts by weight of laureth-7, homogenizing for three minutes, cooling down, feeding the weighed 1 part by weight of tranexamic acid, 0.5 part by weight of essence and 1 part by weight of phenoxyethanol, stirring uniformly, and discharging the obtained material, to obtain the matrix.
2. Preparation of the Borojo skin care product: uniformly mixing and dispersing the Borojo powder in the matrix prepared in the step 1 to obtain a Borojo whitening cream.

Embodiment 8

In one embodiment of the Borojo skin care product of the present invention, except the matrix, the remainder of the skin care product of the embodiment is same as the Embodiment 7. The matrix in the Borojo skin care product of the embodiment comprises the following components in parts by weight: 50 parts of water, 10 parts of glycerin, 10 parts of hydrogenated polydecene, 10 parts of ethylhexyl palmitate, 1 part of butanediol, 1 part of cyclic polydimethylsiloxane, 0.1 part of cetearyl alcohol, 0.1 part of C12-20 alkyl glucoside, 5 parts of C13-14 isoparaffin, 5 parts of PEG-100 stearate, 5 parts of polyacrylamide, 5 parts of polydimethylsiloxane, 0.1 part of laureth-7, 0.1 parts of titanium dioxide, 5 parts of tocopherol acetate, 0.1 part of allantoin, 1 part of xanthan gum, 0.1 part of tranexamic acid, 1 part of essence, 1 part of sodium hyaluronate, and 0.1 part of phenoxyethanol.

Embodiment 9 Experiment about the Anti-Ageing Effect of the Borojo Skin Care Product of the Present Invention 1 Experimental materials and methods
1.1 Experimental materials
1.1.1 Experimental animals: 60 SPF grade KM mice, including half males and half females, weighing 25-30 g, provided by the Experimental Animal Center in Guangzhou University of Chinese Medicine, and having a license number of SCXK (Guangdong)-2013-0020.
1.2 Main instruments: a paraffin embedding machine EG1160 (German LEICA), a microplate reader (Biotek Elx808), a radial microtome RM2255 (German LEICA), a paraffin water bath-slide drier TEC-2500 (German LEICA), a BSA224S electronic analytical balance (Sartorius Scientific Instruments (Beijing) Co., Ltd.), a thermostat water bath cauldron (Shanghai Precision Laboratory Equipment Co., Ltd.), an FJ200-S digital display high-speed dispersion machine (Shanghai Specimen Model Factory), a CP-8000 shaver (Shenzhen Codas Electrical Appliances Co., Ltd.), a Seriesn170 shaver (German BRAUN), a UV-2450 ultraviolet-visible spectrophotometer (Japanese Shimadzu), a TYXH-1 vortex mixer (Shanghai Hannuo Instruments Co., Ltd.), etc.
1.3 Experimental samples:
the blank group represents a group without any medicine and experimental intervention;
the matrix group represents a cosmetic base ingredient (matrix) without Borojo powder;

the Borojo group represents the Borojo skin care product containing the Borojo powder and the matrix;

the positive control group represents the skin care product without Borojo, but containing the positive ingredients and matrix with the effects of anti-anaphylaxis, anti-UV repairing, anti-ageing and whitening confirmed in the market and the matrix; and the Borojo+positive control group represents the skin care product not only containing Borojo, but also containing the positive ingredients and the matrix.

The matrix mentioned above comprises the following components in parts by weight: 50-70 parts of water, 2-10 parts of glycerol, 2-10 parts of caprylic/capric triglyceride, 1-7 parts of titanium dioxide, 1-7 parts of squalane, 0.1-3 parts of C30-45 alkyl dimethicone or polycyclohexene oxide cross-linked polymer, 0.1-3 parts of panthenol, 0.1-3 parts of decamethylcyclopentasiloxane, 0.1-3 parts of cetearyl alcohol, 0.1-3 parts of C12-20-alkyl glucoside, 0.1-3 parts of sodium acrylates copolymer or mineral oil or PPG-1 trideceth-6, 0.1-3 parts of polydimethylsiloxane, 0.1-3 parts of PEG-20 methyl glucose sesquistearate, an appropriate amount of methylisothiazolinone, an appropriate amount of ethylhexylglycerin, 0.01-1 part of carbomer, 0.01-1 part of xanthan gum, 0.01-1 part of triethanolamine, and 0.01-0.2 part of disodium EDTA.

In the Borojo group and Borojo+positive control group mentioned above, the mass concentration of the Borojo powder in the skin care product is 0.1%-5%.

The positive ingredient comprises the following components: tocopherol acetate and retinyl palmitate. In the control group and Borojo+positive control group mentioned above, the mass concentration of tocopheryl acetate in the skin care product is 0.1%-5%, and the mass concentration of retinyl palmitate in the skin care product is 1%.

1.4 Experimental reagents: D-galactose (Shanghai Lanji Technology Development Co., Ltd., Batch Number: 120820); a hydroxyproline kit (alkaline hydrolysis) (Nanjing Jiancheng Bioengineering Institute, Batch Number: 20130806); an ELISA kit for tissue inhibitor of metalloproteinase-1 (TIMP1) in mice (Tianjin Boruikang Biotechnology Company, Batch Number: BRK-E80-8189100801); a non-toxic environmental-protection H-E staining kit (Batch Number: 201307929) purchased from Nanjing Jiancheng Bioengineering Institute; and other chemical reagents being analytically pure.

1.5 Experimental methods 1.5.1 Animal modeling and administration: 60 mice are randomly divided into five groups by weight, including 12 mice in each group. The group A is a blank control group; the group B is a matrix group; the group C is a Borojo-containing group; the group D is a group containing positive medicines; and the group E is a Borojo+positive control group. The hair on the backs of the mice in each group is removed within 24 hours before the experiment, wherein the exposed area is about 4 cm*3 cm. Except the blank control group, 5% of D-galactose (200 mg·kg−1) is subcutaneously injected into napes of the mice in other groups every day, and is continuously injected for 28 days, to establish a subacute ageing model of mice. The blank control group accepts no any processing. Administration is started from the first day of modeling. The group A is not applied with any medicine; the group B is applied with matrix every day; the group C is applied with Borojo-containing cosmetics; the group D is applied with positive medicines; the group E is applied with Borojo+positive cosmetics; each group is applied with a cosmetic sample based on 2 mg/cm² every day and is continuously applied for 28 days; and the mice are killed after 1 hour in the last administration.

1.5.2 Measurement of the content of hydroxyproline in the skin homogenate supernatant: taking circular skin with the diameter of 1.2 cm from each mouse; removing a fat layer; cutting the skin into pieces and then placing the skin in a water bath at 99° C. for 20 min; taking out and cooling the skin with running water; adjusting a PH value; diluting to 10 ml; adding toner and then centrifuging at a speed of 3500 r/min for 10 min, taking the supernatant; fully mixing according to the steps of the instruction; placing the obtained mixture in a spectrophotometer for colorimetric processing at 550 nm; and measuring an absorbance A value of each tube.

The content of hydroxyproline in the skin=[(the absorbance of a measuring tube−the absorbance of a blank tube)/(the absorbance of a standard tube−the absorbance of the blank tube)]/the concentration of the standard tube/the content of protein*a dilution multiple 1.5.3 Measurement of the content of TIMP-1 in the skin homogenate supernatant: taking circular area skin with the diameter of 1.2 cm from each mouse; scraping the fat layer; using a homogenizer to homogenize at a revolution speed of 18000 r/min for 5 min to prepare 1% of homogenate; using a high-speed freezing centrifuge to centrifuge at 16000 r/min for 10 min, and then taking the supernatant for future use; and measuring the concentration of TIMP-1 in the skin tissue homogenate according to the instruction of the ELISA kit.

The content of TIMP-1 in the skin=[(the absorbance of the measuring tube−the absorbance of the blank tube)−c]/b/the content of protein*the dilution multiple Note: c denotes a value c of a standard curve; b denotes a slope of the standard curve.

1.5.4 Histopathological observation: taking another part of skin tissues from each group to be soaked in 10% formalin solution for 2 days; taking out the soaked skin tissues for conventional dehydration; impregnating in paraffin, slicing, and HE staining; observing the epidermal thickness, the tissue structure integrity, the cell stratification and the epidermal synapse clarity of the skin tissues in each group under a microscope; observing the arrangement and distribution conditions of fibrous tissues of a dermal layer, the papillary dermal layer and sebaceous gland atrophy conditions, etc.; and comparing with the morphology of skin tissues of the mice in the group without ageing mode ing in the blank group.

1.5.5 Statistics: all the statistics are completed on DAS1.0 software; the measurement data are represented by $\bar{x}$+/−s; the comparison between the groups is performed by t test; if P<0.05, there is a statistical significance.

1.5.6 Judgment of results: the contents of hydroxyproline and TIMP-1 in different groups are statistically analyzed to observe the differences among the Borojo group and other groups.

2 Results 2.1 General situations of the mice

The mice in each group grow normally; the weight increases steadily; no abnormal obesity and weight loss are found; the daily water drinking and urination are normal; compared with the blank control group, the weight of each group has no significant difference (P>0.05); and the results are shown in Table 1. Compared with the blank group, the mice in each D-galactose subacute ageing modeling mouse group are out of spirits and do not like activities, the hair on the backs grows slowly, and the skin is dark red.

TABLE 1

Change ($\bar{x}$ +/− s, n = 12) of weight (g) of the mice in each group

| Group | 1 d | 14 d | 28 d |
|---|---|---|---|
| Blank group | 28.7 ± 3.3 | 34.5 ± 4.5 | 38.5 ± 6.0 |
| Matrix group | 30.3 ± 4.5 | 36.4 ± 6.7 | 39.8 ± 6.8 |
| Borojo group | 28.8 ± 3.3 | 35.1 ± 4.0 | 38.3 ± 5.8 |
| Positive control group | 30.6 ± 4.3 | 36.6 ± 6.6 | 39.4 ± 7.5 |
| Borojo + positive control group | 30.0 ± 4.0 | 36.3 ± 6.7 | 39.6 ± 7.5 |

2.2 Observation for histopathological morphology of skin tissues in each group 2.2.1 For the mice of the blank control group, the epidermal layer has integral tissue structure, clear cell stratification, normal skin thickness, and obvious furcella; the dermal layer has visible wavy fibrous tissues which are arranged in order, are distributed uniformly and have natural density; and the dermal papillae are clear. The mice of the blank group are free from ageing modeling; and in the microscopic observation, the skin tissues of the mice show normal skin tissue morphology, as shown in FIG. 1.

Figure 2:
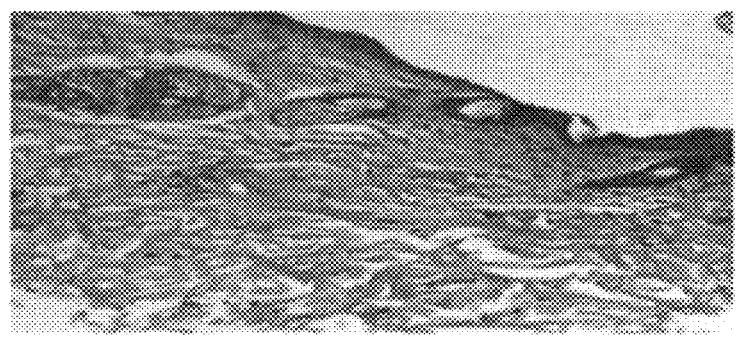
FIG. 2 is the pathological morphology of skin tissues of mice in a matrix group.

2.2.2 In the matrix model group, the epidermal tissues are significantly thinner, the structure is not complete, the stratification is unclear, the dermal-epidermal junction is in a straight line shape, and the furcella disappears; the dermal tissues are disordered in arrangement, uneven in distribution and sparse in structure; dermal papillae are not obvious; and the sebaceous glands and the sweat glands atrophy. The skin tissues of the mice in the matrix group show significant ageing tissue morphology, as shown in FIG. 2.

Figure 3:
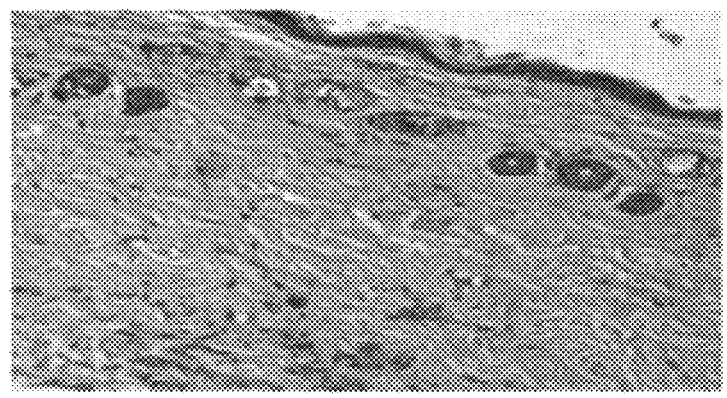
FIG. 3 is the pathological morphology of skin tissues of mice in a Borojo group.
Figure 4:
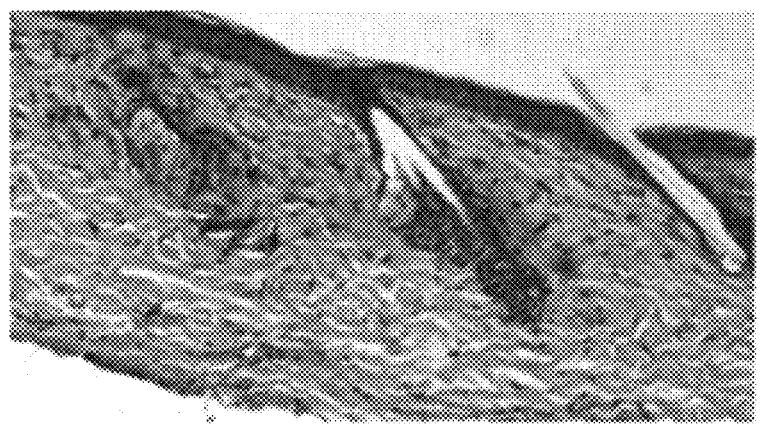
FIG. 4 is the pathological morphology of skin tissues of mice in a positive control group.
Figure 5:
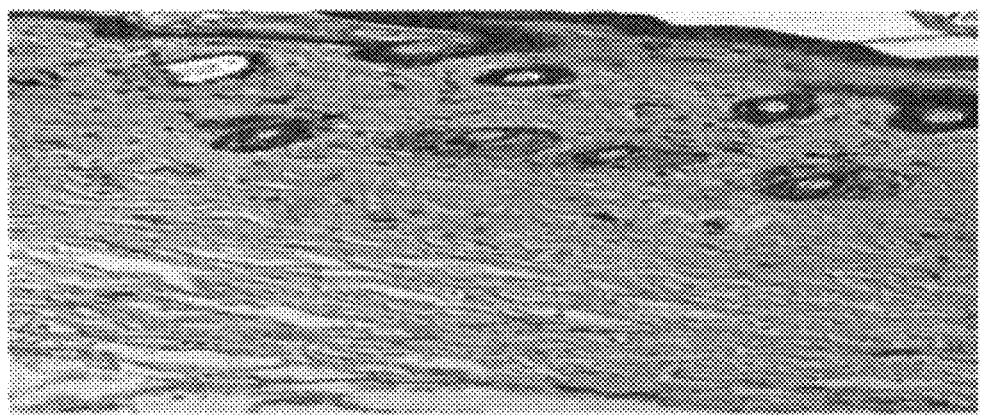
FIG. 5 is the pathological morphology of skin tissues of mice in a Borojo+positive control group.

2.2.3 For the mice of the Borojo group, the positive control group and the Borojo+positive control group, the skin tissues show more consistency in the microscopic observation. The epidermal tissues show mild thinning; the stratification of skin cells is relatively clear; the furcella and dermal papillae are relatively obvious; and the dermal layer has visible wavy fibrous tissues which are arranged in order and are distributed uniformly, and has more sebaceous glands. The Borojo group is shown in FIG. 3; the positive control group is shown in FIG. 4; and the Borojo+positive control group is shown in FIG. 5.

2.3 Measurement results of the concentration of hydroxyproline in the skin of mice: compared with the matrix group, the contents of hydroxyproline in the skin homogenates of the Borojo group, the positive control group and the Borojo+positive control group increase significantly (P<0.05); compared with the blank group, the contents of hydroxyproline in the skin homogenates of the Borojo group, the positive control group and the Borojo+positive control group and those in the normal mice without ageing modeling have no significant difference (P>0.05); in comparison, the concentrations of hydroxyproline of the Borojo group, the positive control group and the Borojo+positive control group have no significant difference (P>0.05). As a result, compared with the normal mice without ageing modeling, the contents of hydroxyproline in the skin homogenates of the ageing mice in the Borojo group, the Borojo+positive control group and the positive control group have no difference (P>0.05). Borojo can make the concentration of hydroxyproline in the skin tissues of the ageing mouse increase significantly, so the possibility and the size of concentration increase are consistent with those of the positive control group and the blank group before ageing modeling; and the concentration increasing effect is not obvious in the Borojo+positive control group through coordinated use.

TABLE 2

Content ($\bar{x}$ +/− s, n = 12) of hydroxyproline in the skin of mice in each group

| Group | Concentration of hydroxyproline (μg · mg$^{-1}$) |
|---|---|
| Blank group | 3.45 ± 0.70[2] |
| Matrix group | 2.41 ± 0.59 |
| Borojo group | 3.49 ± 1.22[1] |
| Positive control group | 3.07 ± 0.84[1] |
| Borojo + positive control group | 3.19 ± 0.71[2] |

Note:
compared with the matrix group, P1 < 0.05, P2 < 0.01.

Conclusion: the cosmetic containing Borojo powder ingredient can significantly increase the content of hydroxyproline in the subcutaneous tissues of the ageing mice, and the concentration of hydroxyproline can reach the content of hydroxyproline in the subcutaneous tissues of the normal mice without ageing.

2.4 Measurement results of TIMP-1 in the skin of mice: Table 3 shows that, compared with the matrix model group, the contents of TIMP-1 in the skin of the Borojo group, the positive control group and the Borojo+positive control group increase significantly (P<0.05); compared with the blank group without modeling, the content of TIMP-1 in the skin of the matrix group decreases significantly (P<0.01), and the concentrations of TIMP-1 in the skin of the Borojo group, the positive control group and the Borojo+positive control group have no significant difference (P>0.05).

Therefore, it can be seen that the matrix model group does not use Borojo and anti-ageing positive substances; and compared with the normal blank group without modeling, the Borojo group, the positive control group and the Borojo+positive control group, the concentration of TIMP-1 in the skin homogenate of the matrix model group decreases significantly. After using the Borojo group and the positive control group, the concentrations of TIMP-1 in the skin of mice increase significantly, and the possibility and size of concentration increase are consistent with those of the positive control group and the blank group before ageing modeling; and the concentration increasing effect is not obvious in the Borojo+positive control group through coordinated use.

TABLE 3

Content ($\bar{x}$ +/− s, n = 12) of TIMP-1 in the skin of mice in each group

| Group | TIMP-1(pg · g$^{-1}$) |
|---|---|
| Blank group | 89.2 ± 32.9[2] |
| Matrix group | 51.4 ± 22.9 |
| Borojo group | 76.2 ± 32.8[1] |
| Postive control group | 74.1 ± 26.3[1] |
| Borojo + positive control group | 77.2 ± 29.3[1] |

Note:
compared with the matrix group, P1 < 0.05, P2 < 0.01.

Conclusions: the cosmetic containing a Borojo powder ingredient can significantly increase the content of TIMP-1 in the subcutaneous tissues of the ageing mice, and the concentration of TIMP-1 can reach the content of TIMP-1 in the subcutaneous tissues of the normal mice without ageing.

3 Discussions and conclusions

In this study, D-galactose-induced ageing mice are compared with normal mice without ageing, to learn about the influence of the use of cosmetics containing the Borojo powder ingredient on the contents of hydroxyproline and TIMP-1 in the skin tissues of the ageing mice. During the experiment, the positive control group and the Borojo+ positive control group are set simultaneously for synergy control. In the study, it is found that the Borojo powder can effectively increase the content of TIMP-1 in the D-galactose-induced ageing skin tissues and effectively increase the content of hydroxyproline in the ageing skin tissues, wherein the action mechanism may be to inhibit the metalloproteinase-induced degradation of skin collagen and promote the proliferation of tissue cells by increasing the secretion and vitality of TIMP-1 in the skin; meanwhile, the Borojo powder can effectively increase the content of main collagen-hydroxyproline in the dermal tissues to become steady. The Borojo powder has a significant effect of resisting the D-galactose-induced skin ageing.

Embodiment 10 Experiment about the Anti-UV Effect of the Borojo Skin Care Product of the Present Invention 1 Experimental materials and methods
1.1 Experimental materials
1.1.1 Experimental animals: 60 SPF grade KM mice, including half males and half females, weighing 18-22 g, provided by the Experimental Animal Center in Guangzhou University of Chinese Medicine, and having the license number of SCXK (Guangdong)-2013-0020.

1.1.2 Main instruments: a ultraviolet high-pressure quartz mercury lamp (which has a power of 125 W and a light wavelength of 300-400 nm, and is produced by Philips (China) Investment Co., Ltd.), the BSA224S electronic analytical balance (Sartorius Scientific Instruments (Beijing) Co., Ltd.), the paraffin embedding machine EG1160 (German LEICA), the radial microtome RM2255 (German LEICA), the paraffin water bath-slide drier TEC-2500 (German LEICA), an inverted optical microscope (Japanese Olympus), the thermostat water bath cauldron (Shanghai Precision Laboratory Equipment Co., Ltd.), the FJ200-S digital display high-speed dispersion machine (Shanghai Specimen Model Factory), the CP-8000 shaver (Shenzhen Codos Electrical Appliances Co., Ltd.), the Seriesn170 shaver (German BRAUN), the UV-2450 ultraviolet-visible spectrophotometer (Japanese Shimadzu), the TYXH-1 vortex mixer (Shanghai Hannuo Instruments Co., Ltd.), etc.

1.1.3 Experimental samples:
the blank group represents a group without any medicine and experimental intervention;
the matrix group represents a cosmetic base ingredient (matrix) without Borojo powder;
the Borojo group represents the Borojo skin care product containing the Borojo powder and the matrix;
the positive control group represents the skin care product without Borojo, but containing positive ingredients with the effects of anti-anaphylaxis, anti-UV repairing, anti-ageing and whitening confirmed in the market and the matrix; and
the Borojo+positive control group represents the skin care product not only containing Borojo, but also containing the positive ingredients and the matrix.

The matrix comprises the following components in parts by weight: 60-80 parts of water, 3-10 parts of cyclic dimethylpolysiloxane, 3-10 parts of C12-15 alkyl benzoate, 3-10 parts of isopropyl myristate, 3-10 parts of propylene glycol, 2-10 parts of glycerin, 1-5 parts of cetearyl alcohol, 1-5 parts of polydimethylsiloxane, 0.5-5 parts of PEG-100 stearate, 0.1-5 parts of PEG-20 methyl glucose sesquistearate, parts of glycerol stearate, 0.1-5 parts of methyl glucose sesquistearate, 0.1-5 parts of tocopherol acetate, 0.3-1 part of polyacrylamide and C13-14 isoparaffin and laureth-7, 0.1-1 part of C12-13 potassium alcohol phosphate, 0.1-1 part of vitamin P or hexadecene copolymer, 0.1-1 part of potassium azelaoyl diglycinate, 0.1-1 part of bis(hydroxymethyl) imidazolidinyl urea and iodopropynyl butylcarbamate, 0.1-1 part of alpha-bisabolol, 0.1-1 part of allantoin, 0.05-0.2 part of methylparaben, 0.1-0.5 part of xanthan gum, 0.05-0.2 part of propylparaben, 0.02-1 part of menthyl lactate, and 0.02-1 part of sweet orange flower oil.

In the Borojo group and the Borojo+positive control group, the mass concentration of the Borojo powder in the skin care product is 0.1%-5%.

The positive ingredient comprises the following components: titanium dioxide, ethylhexyl methoxycinnamate, 4-methylbenzylidene camphor and butyl methoxydibenzoylmethane. In the positive control group and the Borojo+ positive control group, the mass concentration of titanium dioxide in the skin care product is 2%; the mass concentration of ethylhexyl methoxycinnamate in the skin care product is 4%; the mass concentration of 4-methylbenzylidene camphor in the skin care product is 1%; and the mass concentration of butyl methoxydibenzoylmethane in the skin care product is 0.1%-0.5%.

1.1.4 Kits: an SOD kit (Batch Number: 20130906), an MDA kit (Batch Number: 2013006), a Coomassie brilliant blue (Batch Number: 20130918) and the non-toxic environmental-protection HE staining kit (Batch Number: 20130729), wherein all the kits are produced by the Nanjing Jiancheng Bioengineering Institute.

1.2 Methods
12.1 Experimental method: the mice are randomly divided into the blank control group, the matrix group, the Borojo group, the positive control group and the Borojo+ positive control group according to the weight. Before the experiment, the hair on the backs of the mice is removed. The mice in each group are uniformly applied with corresponding skin care product at a dose of 2 mg·cm$^{-2}$; after administration for 25 min, the mice are placed under an ultraviolet lamp and are irradiated, wherein the irradiation time is initially 30 min; the irradiation time is gradually increased every day until the irradiation time is 1 hour, the time is not increased; and the total irradiation time is 14 days. The blank control group is not applied with any medicine, nor irradiated by UV rays.

1.2.2 Preparation of the skin tissue homogenate: after the last administration for 1 hour, killing the mice by cervical dislocation; taking the skin with the area diameter of 1.2 cm each mouse; scraping the fat layer; using the homogenizer to homogenize at the revolution speed of 18000 r/min for 5 mm, to prepare 5% of homogenate; and using the high-speed freezing centrifuge to centrifuge at 16000 r/min for 10 min and then taking the supernatant to spare.

1.2.3 Measurement of the content of MDA in the skin: operating in strict accordance with the instruction of the MDA kit; fully and uniformly mixing the samples; placing the obtained mixture in the water bath at 95° C. for 80 min; taking out and cooling the mixture with running cold water; centrifuging at the speed of 3500 r/min for 10 min; taking the supernatant, using the spectrophotometer for colorimetric processing at 532 nm; and testing the absorbance A value of each tube.

1.2.4 Detection of activity of superoxide dismutase (SOD): diluting the skin homogenate in 1.1.2 5 times to prepare 1% of homogenate; operating in strict accordance with the instruction of the SOD kit; using the spectrophotometer for colorimetric processing at a wavelength of 550 nm; and testing the absorbance A value of each tube.

1.2.5 Histopathological observation of the skin: taking another part of skin tissues from the mice in each group to be soaked in 10% formalin solution for 2 days; taking out the soaked skin tissues for conventional dehydration; impregnating in paraffin, slicing, and HE staining; and observing under the microscope.

1.2.6 Statistics: all the statistics are completed on SPSS13.0 software; the measurement data are represented by $\bar{x}$+/−s; the comparison between the groups is performed by t test; if $P<0.05$, there is a statistical significance.

12.7 Judgment of results

1. The statistical comparison results of difference of vitality of SOD and MDA in the skin homogenate of each group are used for representing the anti-UV-irradiation repairing capacity of the skin of the mice in different groups.

2. The comparison results of changes of the epidermal and dermal structures and the tissue structure of collagen fibers in each group and those in the blank control group are used for judging the anti-UV effect of Borojo.

1.3 Results 1.3.1 Change of Weight

The mice in each group grow well; the weight increases steadily; no abnormal obesity and weight loss are found; the daily water drinking and urination are normal; the mice are in good spirits; compared with the blank control group, the weight of each group has no significant difference ($P>0.05$); and the results are shown in Table 4. After UV irradiation, the mice in each group have mania phenomenon and have strong attack power.

TABLE 4

Change (g, $\bar{x}$ +/− s, n = 12) of the weight of mice in each group

| Group | 0 d | 14 d |
|---|---|---|
| Blank group | 22.9 ± 1.7 | 30.7 ± 2.9 |
| Matrix group | 24.0 ± 1.3 | 32.4 ± 2.3 |
| Borojo group | 23.7 ± 2.5 | 30.1 ± 4.6 |
| Positive control group | 23.8 ± 2.4 | 31.8 ± 2.3 |
| Borojo + positive control group | 22.3 ± 1.5 | 29.7 ± 2.0 |

1.3.2 Skin appearance evaluation

Figure 6:
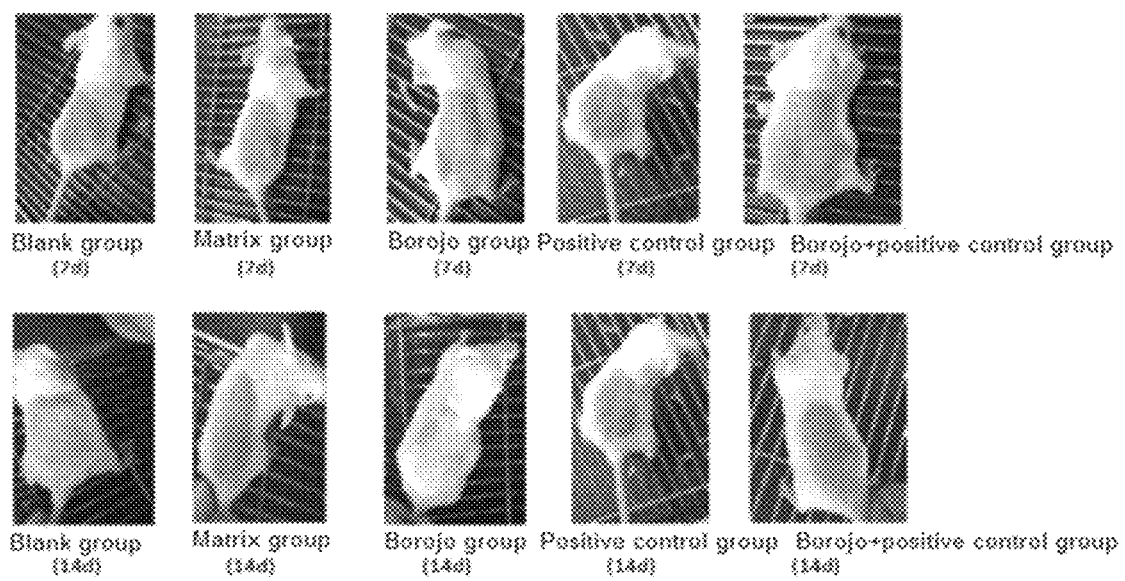
FIG. 6 is a mouse skin appearance evaluation map.

After UV irradiation for 4 days, in the matrix group, an irradiated site begins to show erythema; with the extension of the irradiation time, the area of erythema gradually expands and worsens; and the back has different degrees of wrinkles at the end of the experiment. In the Borojo group and the positive control group, the skin of the back also has mild erythema; with the extension of the experimental time, the skin of the back has a small amount of wrinkles; and Borojo same as the positive ingredients is used and can protect the damage to the skin of mice caused by UV irradiation. In the Borojo+positive control group, the skin of mice has lighter and smaller erythema; a few mice are similar to the blank group; Borojo is used in coordination with the positive ingredients and can make the damage to the skin appearance of the mice caused after UV irradiation get more protection; and the results are shown in FIG. 6.

1.3.3 Borojo significantly increases the content of SOD in the skin homogenate of mice.

Table 5 shows that compared with the matrix group, the content of SOD in the skin homogenate of the Borojo group increases ($P<0.05$), and the contents of SOD in the skin homogenates of the positive control group and the Borojo+positive control group increase significantly ($P<0.01$). Compared with the blank group without UV irradiation, the content of SOD in the skin of the matrix group decreases ($P<0.01$); compared with the blank group, other groups have no significant difference ($P>0.05$); and there is no significant difference among the groups ($P>0.05$). This explains that the UV irradiation causes the decrease of enzyme activity of SOD in the skin of the matrix group, whereas Borojo can significantly inhibit the decrease of enzyme activity of SOD in the skin homogenate of mice caused by the UV irradiation, and the inhibition effect is more significant if the Borojo is used in coordination with other positive ingredients.

TABLE 5

Influence ($\bar{x}$ +/− s) of UV on SOD in the skin of mice in each group

| Group | n (mice) | SOD index value (U/mgprot) |
|---|---|---|
| Matrix group | 12 | 217.6 ± 104.1 |
| Borojo group | 12 | 306.4 ± 77.3[1] |
| Positive control group | 12 | 360.0 ± 109.1[2] |
| Borojo + positive control group | 11 | 398.4 ± 138.5[2] |
| Blank group | 11 | 436.2 ± 219.5[2] |

Note:
compared with the matrix group. P1 < 0.05, P2 < 0.01.

1.3.4 Borojo significantly decreases the content of MDA in the skin homogenate of mice.

Table 6 shows that compared with the matrix group, the Borojo group and the positive control group can decrease the content of MDA in the skin homogenate ($P<0.05$); and the Borojo+positive control group can significantly decrease the content of MDA in the skin homogenate ($P<0.01$); compared with the blank group without UV irradiation, the content of MDA in the skin homogenate of the matrix group increases ($P<0.05$); compared with the blank group without UV irradiation, the Borojo group and the positive control group have no significant difference ($P>0.05$); and there is no significant difference between the groups. The UV irradiation may cause the increase of MDA in the skin homogenate of mice, whereas Borojo can significantly inhibit the increase of MDA in the skin homogenate of mice caused by the UV irradiation, and the inhibition effect is more significant if the Borojo is used in coordination with other positive ingredients.

TABLE 6

Influence ($\bar{x}$ +/− s) of UV on MDA in the skin of mice in each group

| Group | n (mice) | Content of MDA (nmol/ml) |
|---|---|---|
| Matrix group | 12 | 15.4 ± 6.1 |
| Borojo group | 12 | 9.7 ± 6.0[1] |
| Positive control group | 12 | 9.6 ± 3.2[1] |
| Borojo + positive control group | 11 | 8.5 ± 4.5[2] |
| Blank group | 11 | 7.0 ± 4.8[1] |

Note:
compared with the matrix group, P1 < 0.05, P2 < 0.01.

1.3.5 Microscopic results of skin tissue slices of mice

Figure 7A:
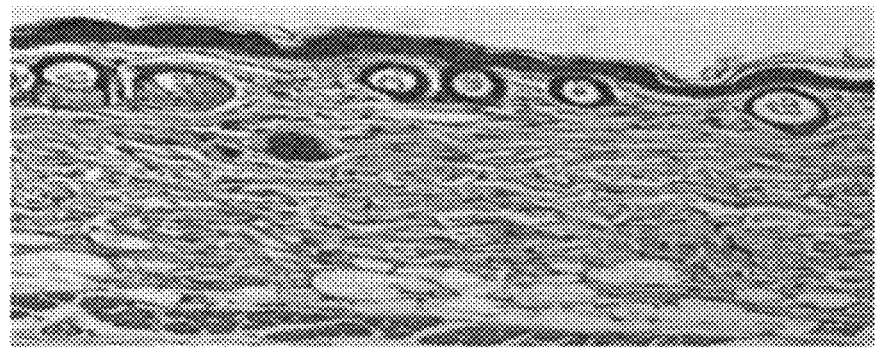
FIGS. 7A, 7B, 7C, 7D, and 7E are series microscopic diagram of mouse skin tissue slices.
Figure 7B:
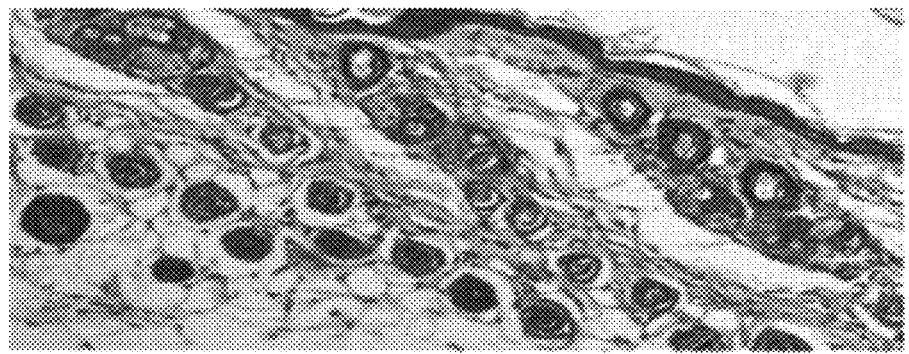
Figure 7C:
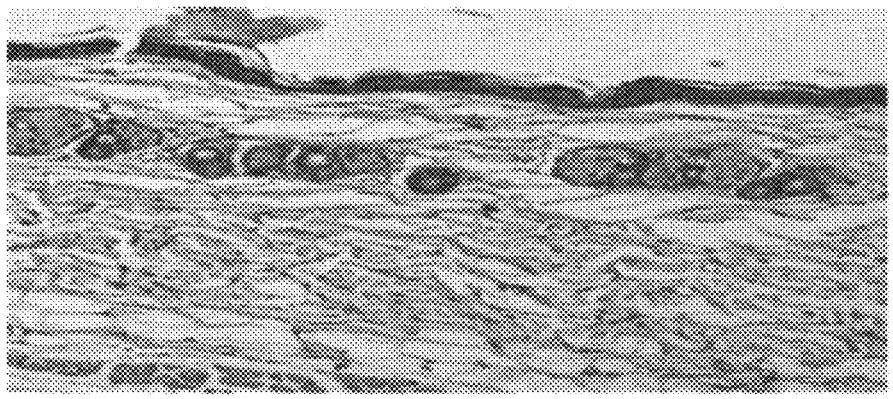
Figure 7D:
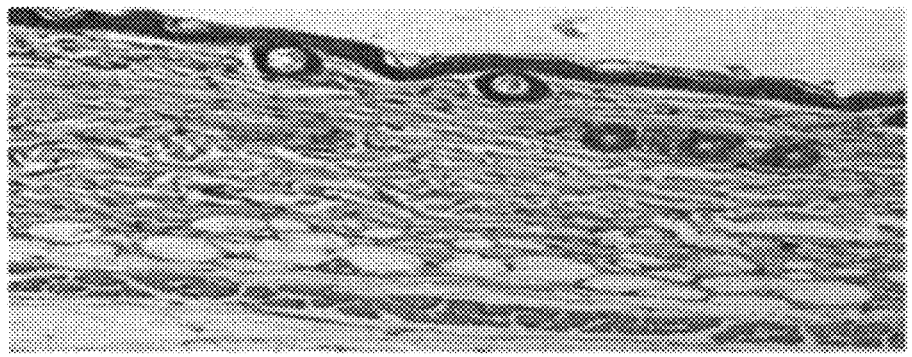

The observation results of the influence of UV on the skin tissues of mice in each group (×100 times under the microscope) are as follows:

Under the microscope, FIGS. 7A and 7D show that the microscopic results of the skin tissues in the blank group without UV irradiation and medicines and the groups using the positive medicines are relatively consistent. The epidermal layer of the skin of mice is integral in structure, thinner, and clear in cell stratification; the skin has obvious furcella and dermal papillae; the dermal layer has visible wavy collagen fiber tissues; and the collagen fibers are uniform in thickness and distribution, and have no phenomenon of obvious fracture and disordered arrangement.

Under the microscope, FIG. 7B shows that the epidermal layer in the matrix group has varying thicknesses, hyperkeratosis, excoriation, and flattened papillary layer; the dermal layer is thickened obviously; the collagen fibers in the dermal layer are thickened, have fracture phenomenon, and are disordered in arrangement; inflammatory cell infiltration is common; and the sebaceous glands have irregular hyperplasia.

Figure 7E:
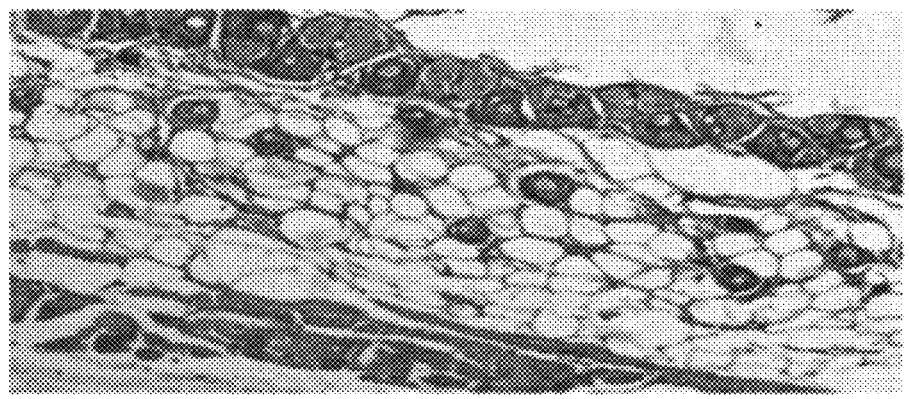

Under the microscope, FIGS. 7C and 7E show that the histological changes are located between the Borojo group and the Borojo+positive control group. Compared with the matrix group, the epidermal layer of the skin of mice in the Borojo group has more integral structure and clearer cell stratification, the dermal layer has visible wavy collagen fibers, and the collagen fibers are more uniform in thickness and distribution and have no phenomenon of obvious fracture and disordered arrangement. The Borojo group and the Borojo+positive control group are relatively consistent. Compared with the Borojo group, the epidermal layers of the skin of mice in the blank group and the positive control group are more integral, and the thickness and distribution of the collagen fibers are more uniform.

1.4 Discussions and conclusions

The experimental results show that the mice is applied with the skin care products containing Borojo, the positive ingredient and a mixture of them both within 25 min before UV irradiation; after UV irradiation, the content of MDA in the skin homogenate of mice increases and decreases significantly, and the activity of SOD decreases and increases significantly, while the matrix group without the substances mentioned above does not have this effect, thereby indicating that Borojo has significant resistance to UV rays.

2 Experiment for measuring SPF value of a Borojo-containing sunscreen cosmetic 2.1 Materials and methods 2.1.1 Test materials: respectively including the matrix group, the Borojo group, the positive control group and the Borojo+positive control group, wherein all the groups are same as 1.1.3 of the embodiment.

2.1.2 UV light source: two ultraviolet high-pressure quartz mercury lamps, which have the power of 125 W and the light wavelength of 300-400 nm, and are produced by Philips (China) Investment Co., Ltd.

2.1.3 UV biometer: UV340A UV spectrophotometer and UV-340A UV illuminometer of LUTRON.

2.1.4 Experimental animals: ordinary grade albino guinea pigs, weighing 250-300 g, provided by the Experimental Animal Center in Guangzhou University of Chinese Medicine, and having the license number of SCXK (Guangdong)-2013-0020.

2.1.5 Experimental method: the hair on the backs of the guinea pigs is removed within 24 hours before the experiment; the Seriesn170 shaver is used for removing the hair on the backs of the guinea pigs; and the preheating is performed for 10 min before irradiation. The UV light source is located right above the irradiated site and is 35 cm away from the irradiated site, wherein the irradiation power is 1346 uw/cm$^2$. The cosmetic in each group is applied throughout the sunscreen region according to the amount of 2 mg/cm$^2$, and the UV irradiation is performed after applying the cosmetic for 25 min.

2.1.5.1 Measurement of minimal MED

The hair on the backs of guinea pigs is removed within 24 hours before the experiment; the opaque medical adhesive plaster is used for covering the back; the medical adhesive plaster is respectively provided with three holes with the diameter of 1.2 cm on both sides of the spine from top to bottom. The animals are placed under UV rays for irradiation and then are irradiated according to the irradiation time of 15 seconds, 19 seconds, 23 seconds, 29 seconds, 36 seconds and 46 seconds (the irradiation time is proportional to the irradiation dose); the medical adhesive plaster is used for respectively covering the holes after irradiating the holes one by one. The irradiated site is observed after irradiation for 16-24 hours; and the minimal irradiation time when faintly visible erythema appears is used as the MED value.

2.1.5.2 Measurement of SPF value: the hair on the backs of guinea pigs is removed within 24 hours before the experiment; an opaque medical adhesive plaster is used for covering the back; the medical adhesive plaster is respectively provided with three holes with the diameter of 1.2 cm on both sides of the spine from top to bottom. The animals are fixed and then placed under the UV lamps for irradiation, and are irradiated according to the irradiation time, the in-vitro experiment SPF values (see Table 7) of cosmetics in each group and a progressive increasing table of irradiation doses of samples in different groups (see Table 8); and the irradiation time is shown in Table 9. The conditions of erythema of each region are observed after irradiation for 16-24 hours; and the minimal irradiation time when faintly visible erythema appears in the applying region is used as the MED value when applying a sunscreen sample.

TABLE 7

Measurement results ($\bar{x}$ +/− s, n = 3) of in-vitro experiment SPF values of cosmetics in each group

| Matrix group | SPF value |
|---|---|
| Borojo group | 17.7 ± 1.6 |
| Positive group | 14.7 ± 2.1 |
| Positive + Borojo group | 21.0 ± 1.0 |

TABLE 8

UV irradiation dose increasing series

| Designed SPF value of the product | Irradiation dose increasing series | | | | | |
|---|---|---|---|---|---|---|
| <8 | 0.64X | 0.80X | 0.90X | 1.00X | 1.10X | 1.25X |
| 8-15 | 0.69X | 0.83X | 0.91X | 1.00X | 1.09X | 1.20X |
| >15 | 0.76X | 0.87X | 0.93X | 1.00X | 1.07X | 1.15X |

TABLE 9

Irradiation time (unit: s) of each hole from top to bottom when applying the cosmetics in each group

| | Irradiation time | | | | | |
|---|---|---|---|---|---|---|
| Group | No. 1 | No. 2 | No. 3 | No. 4 | No. 5 | No. 6 |
| Borojo group | 254 | 291 | 311 | 334 | 357 | 384 |
| positive control group | 212 | 243 | 260 | 279 | 299 | 321 |

TABLE 9-continued

Irradiation time (unit: s) of each hole from top to
bottom when applying the cosmetics in each group

| Group | Irradiation time | | | | | |
|---|---|---|---|---|---|---|
| | No. 1 | No. 2 | No. 3 | No. 4 | No. 5 | No. 6 |
| Borojo + positive control group | 303 | 347 | 371 | 399 | 427 | 459 |

2.1.6 Calculation and judgment of SPF values

SPF=a ratio of MED when applying the sunscreen cosmetics to MED when not applying the sunscreen cosmetics.

The relation between the SPF value and the protection scope is shown in Table 10.

TABLE 10

Relation between the SPF value and the protection
scope as well as the classification of the sunscreen cosmetics

| SPF value | Protection scope | Classification |
|---|---|---|
| 2-3.9 | Minimum | Weak sun protection |
| 4-5.9 | Medium | Medium sun protection |
| 6-7.9 | Good | Good sun protection |
| 8-14.9 | Mmaximum | Excellent sun protection |
| >15 | Super | Super sun protection |

2.2 Results

The MED value of the matrix group is 19 seconds; and the MED value of each animal when applying the cosmetics in each group is shown in Table 11.

TABLE 11

The MED value of each animal when applying
the cosmetics in each group (unit: Ss)

| Group | No. 1 | No. 2 | No. 3 | No. 4 | No. 5 | No. 6 |
|---|---|---|---|---|---|---|
| Borojo group | 256 | 291 | 256 | 291 | 256 | 256 |
| Positive control group | 260 | 260 | 260 | 260 | 321 | 212 |
| Borojo + positive control group | 303 | 303 | 303 | 303 | 371 | 384 |

The SPF values of the cosmetics in each group are calculated according to an SPF calculation formula; and the results are shown in Table 12.

TABLE 12

The SPF values (n = 6) of the cosmetics in each group

| Group | SPF value |
|---|---|
| Borojo group | 14.1 ± 1.0 |
| Positive control group | 13.8 ± 1.8 |
| Borojo + positive control group | 17.2 ± 2.0 |

Conclusions: the anti-UV effect of the Borojo cosmetic belongs to the excellent sun protection; the sun protection effect of the positive group belongs to the excellent sun protection; and the sun protection effect of positive+Borojo group belongs to the super sun protection.

Embodiment 11 Experiment about the
Anti-Anaphylaxis Effect of the Borojo Skin Care
Product of the Present Invention 1. Influence effect of Borojo on immediate type allergy 1.1 Experimental materials 1.1.1 Experimental animals: 60 SPF grade KM mice, including half males and half females, provided by the Laboratory Animal Center in Sun Yat-sen University (University Town), weighing 19.0+/−1.7 g, and having the certificate number of SCXK (Guangdong)-2011-0029.

1.1.2 Main instruments: the BSA2248 electronic analytical balance (Sartorius Scientific Instruments (Beijing) Co., Ltd.), the thermostat water bath cauldron (Shanghai Precision Laboratory Equipment Co., Ltd.), a microplate reader Model680 (Bio-Rad Laboratories Co., Ltd.), a high-speed refrigerated centrifuge KDC-140HR (Anhui USTC Zhongcheng Scientific Instruments Co., Ltd.), the FJ200-S digital display high-speed dispersion machine (Shanghai Specimen Model Factory), and the CP-8000 shaver (Shenzhen Codas Electrical Appliances Co., Ltd.), the Seriesn170 shaver (German BRAUN).

1.1.3 Experimental samples:

the blank group represents a group without any medicine and experimental intervention;

the matrix group represents a cosmetic base ingredient (matrix) without Borojo powder;

the Borojo group represents the Borojo skin care product containing the Borojo powder and the matrix;

the positive control group represents the skin care product without Borojo, but containing positive ingredients with the effects of anti-anaphylaxis, anti-UV repairing, anti-ageing and whitening confirmed in the market and the matrix; and the Borojo+positive control group represents the skin care product not only containing Borojo, but also containing the positive ingredients and the matrix.

The matrix mentioned above comprises the following components in parts by weight: 75-90 parts of water, 1-10 parts of butanediol, 1-10 parts of glycerin, 1-5 parts of beta-glucan, an appropriate amount of phenoxyethanol, 0.05-0.5 part of hydroxyethyl cellulose, 0.05-0.5 part of allantoin, 0.05-0.5 part of disodium EDTA, an appropriate amount of methylparaben, an appropriate amount of PEG-60 hydrogenated castor oil, and an appropriate amount of essence.

In the Borojo group and the Borojo+positive control group, the mass concentration of the Borojo powder in the skin care product is 0.1%-5%.

The positive ingredient comprises the following component: an extract of Chamaenerion Angustifolium flowers or leaves or stems. In the positive control group and the Borojo+positive control group, the mass concentration of the extract of Chamaenerion Angustifolium flowers or leaves or stems in the skin care product is 1.5%.

1.1.4 Positive sensitizer for mice: 4-aminopyridine, a product of Merck Company, having the batch number of 54914223, and prepared into 0.01 mL/g of 0.02% solution with the normal saline before use.

1.1.5 Experimental kit of histamine: a mouse HISElisa kit E-20451, produced by Beijing Yonghui Technology Co., Ltd., and having the batch number of 201306.

12 Methods 12.1 Experimental method 1.2.1.1 Experiment about the influence of mouse skin 4-AP-induced itch mode on an itch threshold The mice are randomly divided into the blank group, the matrix group, the Borojo group, the positive control group and the Borojo+positive control group 2 cm×3 cm area of hair on the back of a mouse is removed by using a shaver; a test fluid is uniformly applied to the skin of the hair-shaved region once a day in a dose of 100 μL per mouse and is continuously applied for 7 days; and the blank group is not given any medicine. After the last administration for 40 min, 0.01 mL/g of 4-aminopyridine (prepared into 0.02% with normal saline) solution is subcutaneously injected into the medicine-applied sites of the napes of the mice; and the normal saline is injected into the blank group. The licking times of each group within 10 min are recorded; and a response inhibition rate is calculated.

Recording standard: the actions that the mouse scratches the head and cheeks with forepaws, scratches the body with hind paws, and bites a parts of the whole body with the mouth are considered as the characteristics for itching every time; the action that the mouse has continuous itching until a brief pause appears is calculated as once itching. Requirements for the brief pause are that the length of time is not considered when the mouse walks, heads out, stands upright, smells something or does other move actions; the actions of repeatedly turning around, licking hands or washing face are not considered as pause.

1.2.1.2 Measurement of the content of histamine: killing the mice after the experiment of relieving itching by cervical dislocation at once; cutting off about 1.5 cm×2 cm area of sensitized skin of the same site, to prepare a tissue homogenate; using the high-speed freezing centrifuge to centrifuge at 16000 r/min for 15 min and then taking the supernatant; and using an Elisa (Enzyme Linked Immunosorbent Assay) kit for measuring the concentration of histamine in the tissue homogenate.

Judgment of the results: the statistical results of an animal licking response inhibition rate and the concentration of histamine in the skin homogenate of animals in each group are used as indicators for the observation of an itching-relieving effect of Borojo on the 4-aminopyridine-induced itching.

1.2.1.3 Statistical method: all the statistics are completed on SPSS 13.0 software; the measurement data are represented by $\bar{x}+/-s$; the comparison between the groups is performed by t test; if P<0.05, there is a statistical significance.

1.3 Results 1.3.1 Change of weight

The KM mice in each group grow well; the weight increases steadily; no abnormal obesity and weight loss are found; the daily water drinking and urination are normal; the mice are in good spirits; compared with the blank control group, the weight of each group has no significant difference (P>0.05); the results are shown in Table 13.

TABLE 13

Change ($\bar{x}+/-s$, unit: g) of weight of the KM mice in each group at different time

| Group | Number | 1 d | 7 d |
|---|---|---|---|
| Blank group | 12 | 20.6 ± 2.4 | 25.4 ± 3.3 |
| Matrix group | 12 | 19.9 ± 2.5 | 24.9 ± 3.2 |
| Borojo group | 12 | 19.3 ± 1.7 | 24.5 ± 3.2 |
| Positive control group | 12 | 19.7 ± 1.3 | 25.0 ± 3.5 |
| Borojo + positive control group | 12 | 19.8 ± 1.9 | 24.9 ± 1.7 |

1.3.2 Borojo has significant inhibition effect on the mice licking response.

Table 14 shows that, compared with the blank group and the matrix group, the Borojo group, the positive control group and the Borojo+positive control group have significant inhibition effect on the mice licking response (P<0.01), wherein the inhibition effect of the Borojo group on the 4-AP-induced mice licking response is strongest and is 52.1%; that of the Borojo+positive control group is 46.9%; that of the positive control group is 46.4%; that of the matrix group is 22.7%; and there is no significant difference between the matrix group and the blank group (P>0.05).

TABLE 14

Influence of anti-anaphylaxis essence of each group on 4-AP-induced mice licking response ($\bar{x}+/-s$)

| Group | Number of animals | Number of licking responses within 10 min | Licking response inhibition rate (%) |
|---|---|---|---|
| Blank group | 12 | 52.4 ± 20.8 | — |
| Matrix group | 12 | 40.5 ± 6.1 | 22.7 |
| Borojo group | 12 | 25.1 ± 4.6[1)*] | 52.1 |
| Positive control group | 12 | 28.1 ± 10.5[1)*] | 46.4 |
| Borojo + positive control group | 12 | 27.8 ± 12.0[1)*] | 46.9 |

Note:
compared with the blank group, [1)]P < 0.01; and compared with the matrix control group, *P < 0.01.

1.3.3 Borojo has significant inhibition effect on the content of histamine in the skin of allergic animals.

Table 15 shows that, compared with the blank group, the Borojo group, the positive control group and the Borojo+positive control group have significant inhibition effect on the content of histamine in the skin of mice (P<0.05), wherein the inhibition effect of the positive control group is strongest; and compared with the positive control group and the Borojo group, the inhibition effect of the Borojo+positive control group on histamine in the skin has no significant difference (P>0.05).

TABLE 15

Inhibition effect ($\bar{x}+/-s$) of each group on the content of histamine in 4-AP-induced mouse skin

| Group | Number of animals (n) | Concentration of histamine in the skin (μg/kg) |
|---|---|---|
| Blank group | 12 | 634.8 ± 113.8 |
| Matrix group | 12 | 613.3 ± 220.0 |
| Borojo group | 12 | 516.7 ± 122.4* |
| Positive control group | 12 | 494.3 ± 167.8* |
| Borojo + positive control group | 12 | 523.8 ± 109.2* |

Note:
1. Compared with the blank group, *P < 0.05.

1.4 Discussions and conclusions

In the experiment, the mouse skin 4-AP-induced itching model is chosen to study the influence of Borojo on immediate type allergy. The results show that the Borojo group can significantly decrease the 4-AP-induced itching threshold for mice, and has the effects of significantly preventing 4-AR-induced mouse skin itching and effectively reducing the concentration of histamine in the skin.

2. Experiment about the effect of Borojo on dinitrofluorobenzene-induced delayed-type hypersensitivity in mice 2.1 Experimental materials 2.1.1 Experimental animals: 60 SPF grade KM mice, including half males and half females, provided by the Experimental Animal Center in Guangzhou University of Chinese Medicine, weighing 22.2+/−1.9 g, and having the license number of SCXK (Guangdong)-2008-0020.

2.1.2 Main instruments: the BSA224S electronic analytical balance (Sartorius Scientific Instruments (Beijing) Co., Ltd.), the CP-8000 shaver (Shenzhen Codos Electrical Appliances Co., Ltd.), the Seriesn170 shaver (German BRAUN), and a 6 mm metal puncher.

2.1.3 Medicines and reagents 2.1.3.1 The experimental samples are same as 1.1.3.1 of the embodiment.

2.1.3.2 Reagents: a positive sensitizer for mice: 2, 4-dinitro-chlorobenzene (DNCB), Shanghai Jingchun Reagents Co., Ltd., Batch Number: 9085.

2.2 Methods 2.2.1 Experimental method: the mice are randomly divided into the blank group, the matrix group, the Borojo group, the positive control group and the Borojo+positive control group according to the weight. 2 cm×3 cm area of hair on the back and abdomen of each mouse is removed with the shaver.

Abdominal sensitization: after 24 hours, the abdomens of the animals in each group are applied with 50 μL of 5% 2, 4-dinitro-chlorobenzene (DNCB) acetone solution for sensitizing the animals; and the corresponding medicines are applied on the hair-shaved regions of the backs in each group once a day in a dose of 100 μL per animal and are continuously applied for 7 days.

Ear Sensitization: after the last administration for 1 hour in the abdominal sensitization, 1% DNcB is uniformly applied on right ears of the mice in each group for attacking. After attacking for 24 hours, the mice is killed by dislocation; the metal puncher with the diameter of 6 mm is used for punching sites which are located at the middles of double ears of the mice and are 1 mm away from the ear roots; the ear tissues punched by the puncher are taken to be precisely weighed by a sensitive balance; and the difference between the weights of a left ear slice and right ear slice is used as a swelling degree. Meanwhile, the thorax and abdomen are opened to take out and weigh the thymus and spleen of each mouse; and the spleen weight (mg) and thymus weight (mg) of every 10 g of mouse are respectively used as a spleen index and a thymus index.

Judgment of the results: the increased or decreased data of the ear swelling degrees, the spleen indexes and the thymus indexes of the mice in each group are compared statistically; and the results are used as the indicators of enhancement or inhibition of Borojo on delayed type allergy experiment positivity.

2.2.2 Statistics: all the statistics are completed on the SPSS13.0 software; the measurement data are represented by $\bar{x}$+/−s; the comparison between the groups is performed by t test; if $P<0.05$, there is a statistical significance.

2.3 Experimental results 2.3.1 Change of weight

The mice in each group grow well; the weight increases steadily; no abnormal obesity and weight loss are found; the daily water drinking and urination are normal; the mice are in good spirits; and compared with the blank control group, the weight of each group has no significant difference ($P>0.05$); and the results are shown in Table 16.

TABLE 16

Change ($\bar{x}$ +/− s, n = 12) of the weight (g) of mice in each group

| Group | 1 d | 7 d |
|---|---|---|
| Blank group | 24.7 ± 3.0 | 29.5 ± 4.3 |
| Matrix group | 25.5 ± 2.8 | 28.5 ± 4.4 |
| Borojo group | 25.6 ± 2.3 | 29.2 ± 3.3 |
| Positive control group | 24.6 ± 2.4 | 29.6 ± 2.9 |
| Borojo + positive control group | 25.8 ± 2.7 | 28.9 ± 3.7 |

2.3.2 Results of delayed type hypersensitivity reaction in mice (see table 17)

2.3.2.1 After the allergy is stimulated for 24 hours on the right ears of the mice in each group, it is visible to naked eyes that the right ears of the mice swell, are obviously thickened and have congestion. Compared with the blank group, the measurement results of the swelling degrees of the ears of mice in each group have no difference ($P>0.05$).

2.3.2.2 Compared with the blank group, the thymus index of the Borojo group has no difference ($P>0.05$); and the thymus indexes of the other three groups are compared and have no significant difference ($P>0.05$). This indicates that the change of thymus index caused by Borojo to the delayed type hypersensitivity reaction in animals is consistent with that of the blank group.

2.3.2.3 Compared with the blank group, the spleen index of the Borojo group is significantly smaller than that of the blank group and the other three groups, thereby indicating that Borojo has significant inhibition effect on the increase of the spleen index caused by the delayed type hypersensitivity reaction in animals ($P<0.05$). In comparison, the other groups have no difference ($P>0.05$).

TABLE 17

Results ($\bar{x}$ +/− s) of medicines in each group to the delayed type hypersensitivity reaction in mice

| Group | Number of animals | Ear swelling difference (mg) | Thymus index (%) | Spleen index (%) |
|---|---|---|---|---|
| Blank group | 11 | 3.9 ± 2.1 | 31.4 ± 10.6 | 46.6 ± 12.4 |
| Matrix group | 11 | 4.9 ± 3.7 | 27.6 ± 9.1 | 43.5 ± 9.0 |
| Borojo group | 12 | 4.7 ± 2.1 | 31.0 ± 12.6 | 36.2 ± 8.7* |
| Positive control group | 12 | 4.6 ± 3.7 | 27.0 ± 10.8 | 42.9 ± 10.5 |
| Borojo + positive control group | 12 | 4.1 ± 2.6 | 27.4 ± 10.3 | 43.7 ± 10.3 |

Note:
compared with the blank group, *$P < 0.05$.

3. Discussions and conclusions

Compared with other groups, the Borojo group has significant difference in the inhibition effect of the spleen, and the inhibition results of the other groups are consistent. This indicates that Borojo has significant inhibition effect on the increase of the spleen index caused by the delayed type hypersensitivity reaction, but does not have significant influence on the other thymus indexes and ear swelling effects.

Embodiment 12 Experiment about the Whitening Effect of the Borojo Skin Care Product of the Present Invention 1. In-vitro experiment 1.1 Experimental materials 1.1.1 Main instruments: the BSA2248 electronic analytical balance (Sartorius Scientific Instruments (Beijing) Co., Ltd.), the thermostat water bath cauldron (Shanghai Precision Laboratory Equipment Co., Ltd.), and the UV-2450 ultraviolet-visible spectrophotometer (Japanese Shimadzu).

1.1.2 Medicines and reagents 1.1.2.1 Experimental samples: Borojo powder 1.1.2.2 Experimental reagents and preparation A. Tyrosinase (Manufacturer: Worthington; Specifications: 500 U/mg; Batch Number: LS003789). 5 mg of tyrosinase is weighed precisely, is placed in a 25 ml volumetric flask, is diluted to the mark by using a PBS buffer solution with the PH of 7.2, and then is prepared into a solution with the tyrosinase activity of 100 U, so as to obtain the tyrosinase.

B. L-dopa (Manufacturer: Worthington; Specifications: >99%; Batch Number: FBA169). 0.03750 g of L-dopa is weighed precisely, is placed in the 25 ml volumetric flask, is diluted to the mark by using the PBS buffer solution with the PH of 7.2, and then is prepared into 0.15% L-dopa solution, so as to obtain the L-dopa.

C. Preparation of Sample Solutions

Preparation of a 1% sample solution: 100 mg of Borojo powder is weighed precisely, is placed in a 10 ml volumetric flask, is diluted to the mark by using the PBS buffer solution with the PH of 7.2, and then is prepared into the 1% sample solution.

Preparation of a 3% sample solution: 300 mg of Borojo powder is weighed precisely, is placed in the 10 ml volumetric flask, is diluted to the mark by using the PBS buffer solution with the PH of 7.2, and then is prepared into the 3% sample solution.

Preparation of a 5% sample solution: 500 mg of Borojo powder is weighed precisely, is placed in the 10 ml volumetric flask, is diluted to the mark by using the PBS buffer solution with the PH of 7.2, and then is prepared into the 5% sample solution.

Preparation of a 7% sample solution: 700 mg of Borojo powder is weighed precisely, is placed in the 10 ml volumetric flask, is diluted to the mark by using the PBS buffer solution with the PH of 7.2, and then is prepared into the 7% sample solution.

Preparation of a 9% sample solution: 900 mg of Borojo powder is weighed precisely, is placed in the 10 ml volumetric flask, is diluted to the mark by using the PBS buffer solution with the PH of 7.2, and then is prepared into the 9% sample solution.

1.2 Methods 1.2.1 Measurement of in-vitro tyrosinase activity

Taking corresponding samples according to Table "1.1.2.2"; and measuring the tyrosinase inhibition effect of the sample solutions corresponding to the samples in each group according to the following testing method:

a test sample A: 3 mL of PBS+0.5 mL of tyrosinase solution;

a test sample B: 3.5 mL of PBS;

a test sample C: 1 mL of sample solution+2 mL of PBS+0.5 mL of tyrosinase solution;

a test sample D: 1 mL of sample solution+2.5 mL of PBS.

Simultaneously preparing four test sample solutions A, B, C and D; then respectively adding 0.5 mL of 0.15% L-dopa solution immediately; reacting at a constant temperature of 37° C. for 5 min; and measuring the absorbance value at 475 nm.

Tyrosinase inhibition rate $(\%)=[(A-B)-(C-D)]/(A-B) \times 100$

Note: the sample solutions are respectively: 1%, 3%, 5%, 7% and 9% Borojo powder solutions.

1.2.2 Statistics: all the statistics are completed on SPSS19.0 software; the measurement data are represented by $\bar{x}+/-s$; the comparison between the groups is performed by t test; if $P<0.05$, there is a statistical significance.

1.3 Results

Figure 8:
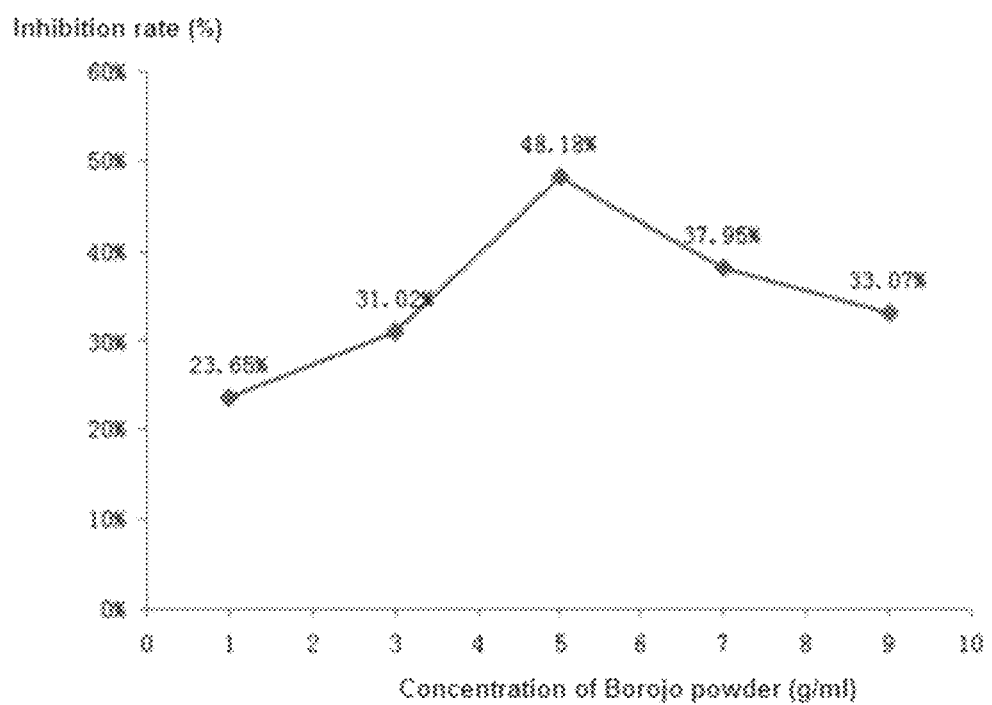
FIG. 8 shows an inhibiting effect of the Borojo powder at different concentrations on tyrosinase activity.
Figure 9:
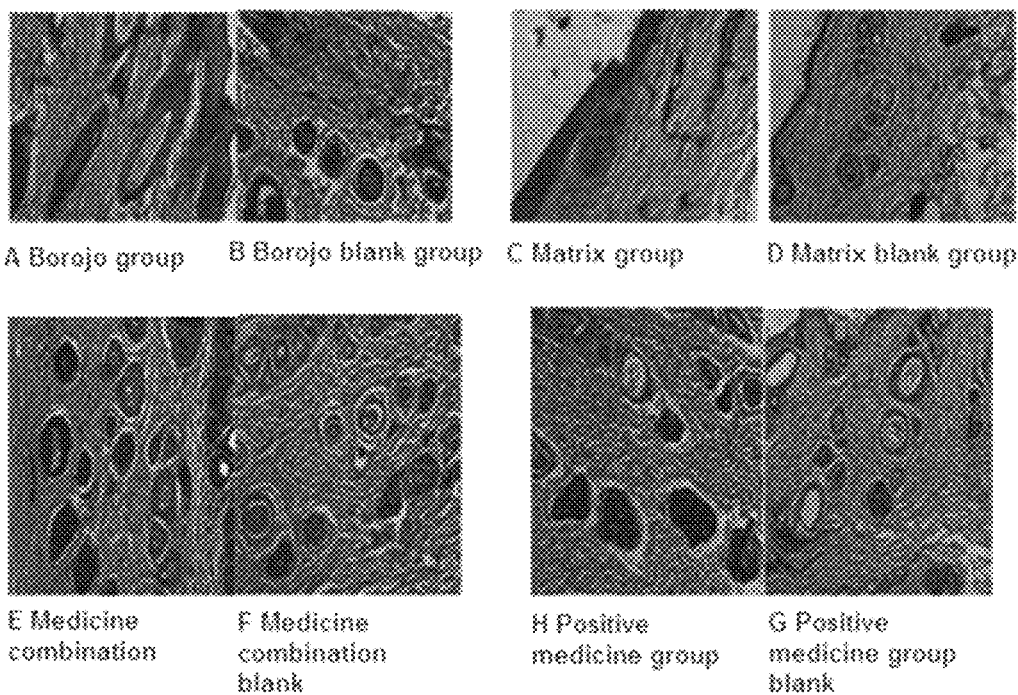
FIG. 9 is a staining comparison diagram (*100 times) of skin slices of pigmented guinea pigs after applying medicines.

Table 18 and FIG. 8 show that different concentrations of Borojo have significant inhibition effect on the activity of tyrosinase; with the increasing of the concentration, the tyrosinase activity inhibition effect shows an increasing trend; when the concentration of Borojo is 5%, the inhibition rate is 48.18%; and with the continuous increasing of the concentration of Borojo, the tyrosinase activity inhibition effect weakens gradually.

TABLE 18

Inhibition conditions ($\bar{x}$ +/− s, n = 4) of different concentrations of Borojo samples to the tyrosinase activity

| Concentration of Borojo (%) | Tyrosinase activity inhibition rate (%) |
|---|---|
| 1 | 23.65 ± 0.15 |
| 3 | 31.02 ± 0.25 |
| 5 | 48.18 ± 0.15 |
| 7 | 37.95 ± 0.31 |
| 9 | 33.07 ± 0.16 |

1.4 Conclusions: In-vitro studies indicate that Borojo at the concentration of 0.1%-9% has an obvious inhibition effect on tyrosinase activity, and has a strongest effect at the concentration of 5%.

2 Animal experiment 2.1 Experimental materials 2.11 Experimental animals: 12 ordinary grade female pigment guinea pigs, weighing 194.7+/−23.2 g, and provided by the Experimental Animal Center in Guangzhou University of Chinese Medicine.

21.2 Main instruments: the CP-8000 shaver (Shenzhen Codos Electrical Appliances Co., Ltd.), the Seriesn170 shaver (German BRAUN), the radial microtome RM2255 (German LEICA), the paraffin embedding machine EG1160 (German LEICA), and the paraffin water bath-slide drier TEC-2500 (German LEICA).

2.1.3 Medicines and reagents 2.1.3.1 Experimental samples:

the matrix group represents a cosmetic base ingredient (matrix) without Borojo powder;

the Borojo group represents the Borojo skin care product containing the Borojo powder and the matrix;

the positive control group represents the skin care product without Borojo, but containing positive ingredients with the effects of anti-anaphylaxis, anti-UV repairing, anti-ageing and whitening confirmed in the market and the matrix; and the Borojo+positive control group represents the skin care product not only containing Borojo, but also containing the positive ingredients and the matrix.

The matrix comprises the following components in parts by weight: 50-70 parts of water, 1-10 parts of glycerin, 1-10 parts of hydrogenated polydecene, 1-10 parts of ethylhexyl palmitate, 1-10 parts of butanediol, 1-10 parts of cyclic polydimethylsiloxane, 0.1-5 parts of cetearyl alcohol, 0.1-5 parts of C12-20 alkyl glucoside, 0.1-5 parts of C13-14 isoparaffin, 0.1-5 parts of PEG-100 stearate, 0.1-5 parts of polyacrylamide, 0.1-5 parts of polydimethylsiloxane, 0.1-5 parts of laureth-7, 0.1-5 parts of titanium dioxide, 0.1-5 parts of tocopherol acetate, 0.1-1 part of allantoin, 0.1-1 part of xanthan gum, 0.1-1 part of tranexamic acid, an appropriate amount of essence, 0.1-1 part of sodium hyaluronate, 0.1-1 part of phenoxyethanol.

In the Borojo group and Borojo+positive control group mentioned above, the mass concentration of the Borojo powder in the skin care product is 0.1%-5%.

The positive ingredient comprises the following components: tranexamic acid, ethyl ascorbic acid, nicotinamide, alpha-bisabolol and ceramide. In the positive control group and Borojo+positive control group mentioned above, the mass concentration of tranexamic acid in the skin care product is 0.1%; the mass concentration of ethyl ascorbic acid in the skin care product is 0.1%; the mass concentration of nicotinamide in the skin care product is 2%; the mass concentration of alpha-bisabolol in the skin care product is 0.1%; and the mass concentration of ceramide in the skin care product is 0.5%.

2.1.3.2 Reagent: L-dopa (Manufacturer: Worthington; Specifications: >99%; Batch Number: FBA189).

2.2 Methods 2.2.1 Grouping and medicine test

The 12 pigment guinea pigs are randomly divided into four groups, respectively including the matrix group (a), the Borojo group (b), the positive control group (c), and the Borojo positive control group (d). The shaver is used for shaving two regions with the size of a bout 2 cm×2 cm on each guinea pig, wherein one region is used as a medicine-applying region, and the other one receives no any processing and is not applied with any medicine. The corresponding medicines (medicines contained in a, b, c and d) are uniformly applied on the skin of the medicine-applying regions by using cotton swabs according to the grouping conditions, respectively, at a dose of 0.2 mg/cm$^2$, twice a day. Before applying the medicines every time, the hair on the backs of the guinea pigs should be shaved with the shaver; after continuously applying the medicines for 30 days, the skin tissues are taken, are fixed by 10% neutral formalin solution, and are subjected to conventional paraffin section processing.

2.2.2 Staining and preparation of slices

Tissue slices are deparaffinated, are soaked with 0.1% L-dopa solution for 4 hours, are rinsed with a buffer solution, and are subjected to conventional HE staining. After staining, the tissue slices are observed by using a microscope and are photographed; and the optical density is analyzed.

2.2.3 Measurement of the optical density

The stained slices are photographed by using the microscope; then the image is analyzed by using ImageproPlus6.0 software; each sample is photographed randomly to obtain 15 photos for analyzing the optical density; and an average value of the optical density is used for representing the content of melanin. The amount of melanin in the slices is closely related to the average value of optical density; the higher the average value of optical density is, the higher the relative value of the content of melanin in the skin is; on the contrary, the lower the average value of optical density is, the lower the relative value of the content of melanin in the skin is.

Inhibition rate for the average value of optical density=(the blank average value of optical density–the average value of optical density of the medicine-applying group)/the blank average value of optical density*100%

2.2.4 Statistics: all the statistics are completed on the SPSS19.0 software; the measurement data are represented by x̄+/−s; the comparison between the groups is performed by t test; if P<0.05, there is a statistical significance.

2.2.5 Judgment of results

Tyrosinase inhibition rate (%)=[(A−B)−(C−D)]/(A−B)×100

Inhibition rate for the average value of optical density of the groups=(the blank average value of optical density of the groups–the average value of optical density of the cosmetics of groups)/the blank average value of optical density of the groups*100%

The differences of the inhibition rates for optical density value between the groups are compared and are used as the indicators for judging the effect that the Borojo cosmetics inhibit tyrosinase and reduce the generation of melanin.

2.3 Results 2.3.1 Change of weight

The guinea pigs in each group grow well; the weight increases steadily; no abnormal obesity and weight loss are found; the daily water drinking and urination are normal; and the guinea pigs are in good spirits.

TABLE 19

Change (x̄ +/− s, n = 3, unit: g) of the weight of pigment guinea pigs at different time

| Number of days (d) | Matrix group | Borojo group | Positive control group | Borojo + positive control group |
|---|---|---|---|---|
| 1 | 231.2 ± 22.8 | 180.7 ± 11.2 | 197.8 ± 3.30 | 214.8 ± 4.50 |
| 7 | 263.3 ± 26.8 | 195.8 ± 18.5 | 219.3 ± 6.50 | 240.2 ± 6.80 |
| 14 | 290.3 ± 33.1 | 230.0 ± 12.8 | 269.0 ± 11.7 | 283.3 ± 5.40 |
| 21 | 323.0 ± 23.5 | 281.0 ± 13.0 | 302.7 ± 13.6 | 316.2 ± 11.9 |
| 28 | 346.8 ± 39.4 | 306.8 ± 18.8 | 310.7 ± 19.4 | 350.2 ± 20.7 |

2.3.2 Results about Borojo inhibiting tyrosinase to reduce melanin and the optical density of slices Table 20 shows that the skin of guinea pigs is continuously applied with medicines for 30 days; and compared with the corresponding blank region, the medicine-applying region of the matrix group has no significant difference (P>0.05), thereby indicating that the matrix group has no whitening effect on the skin. Compared with the blank region, the average values of optical density of the slices in the Borojo group, the positive control group and the Borojo+ positive control group are significantly reduced (P<0.01), thereby indicating that the Borojo group, the positive control group and the Borojo+positive control group can reduce the content of melanin in the skin, wherein compared with the blank skin region, the inhibition rates for the optical density value of the Borojo group, the positive control group and the Borojo+positive control group are respectively 37.21%, 50.47% and 66.38%, thereby indicating that Borojo is used in combination with the positive ingredient and has better effects for collaboratively reducing the level of melanin in the skin.

Inhibition rate for the average value of optical density=(the blank average value of optical density–the average value of optical density of the medicine-applying groups)/the blank average value of optical density*100%

TABLE 20

Inhibition rate (%) for the average value of optical density after applying Borojo

| Group | Blank region (n = 15) | Medicine-applying region (n = 15) | Inhibition effect (%) |
|---|---|---|---|
| Matrix group | 0.1819 ± 0.01824 | 0.1813 ± 0.03111 | / |
| Borojo group | 0.2427 ± 0.02364 | 0.1524 ± 0.04029*** | 37.21% |
| Positive control group | 0.0903 ± 0.03008 | 0.1823 ± 0.01501** | 50.47% |
| Borojo + positive control group | 0.2332 ± 0.01266 | 0.0784 ± 0.01341** | 66.38% |

Note:
Each group is compared with the optical density value of the blank region: *P < 0.05, **P < 0.01.

3 Discussions and conclusions

In the experimental studies, it is found that Borojo has significant activity for inhibiting in-vitro tyrosinase, can effectively prevent L-tyrosine from hydroxylating into dopaquinone, and block the formation of melanin, to achieve the whitening effect. For the animals, the effect is strongest when the concentration of the Borojo powder ingredient is 5%. For the animals, Borojo at the concentration of 0.1%-9% also has the effects of significantly inhibiting the activity of tyrosinase and reducing the generation of melanin, to achieve the significant whitening effect in bodies of the animals.

In the experiments, it is also found that Borojo is used in combination with other whitening substances, and is possible to collaboratively enhance the inhibition for the generation of melanin in the bodies of the animals, to achieve the whitening effect.

Embodiment 13 Experiment about the Moisturizing Effect of the Borojo Skin Care Product of the Present Invention The Borojo skin care product used in the embodiment comprises the Borojo powder and the matrix, wherein the matrix comprises the following components in parts by weight: 50-70 parts of water, 2-10 parts of glycerol, 2-10 parts of caprylic or capric triglyceride, 1-7 parts of titanium dioxide, 1-7 parts of squalane, 0.1-3 parts of C30-45 alkyl dimethicone or polycyclohexene oxide cross-linked polymer, 0.1-3 parts of panthenol, 0.1-3 parts of decamethylcyclopentasiloxane, 0.1-3 parts of cetearyl alcohol, 0.1-3 parts of C12-20-alkyl glucoside, 0.1-3 parts of sodium acrylates copolymer or mineral oil or PPG-1 trideceth-6, 0.1-3 parts of polydimethylsiloxane, 0.1-3 parts of PEG-20 methyl glucose sesquistearate, an appropriate amount of methylisothiazolinone, an appropriate amount of ethylhexylglycerin, 0.01-1 part of carbomer, 0.01-1 part of xanthan gum, 0.01-1 part of triethanolamine, and 0.01-0.2 part of disodium EDTA. The mass concentration of the Borojo powder in the skin care product is 0.1%-5%.

10 female volunteers are selected randomly; the Borojo skin care product of the embodiment is respectively applied on the outer sides (site A) of corners of left eyes, the lower edges (site B) of corners of left eyes, the outer sides (site C) of corners of right eyes and the lower edges (site D) of corners of right eyes of the volunteers for 30 days; the moisture content and moisture loss of the skin of the four sites are detected; and the results are shown in Table 21.

TABLE 21

Comparison ($\bar{x}$ +/− SD, n = 10) of the moisture content and moisture loss of the skin

| | | Moisture content | | Moisture loss | |
|---|---|---|---|---|---|
| Site | Time | Average value +/− standard deviation | Change rate (%) | Average value +/− standard deviation | Change rate (%) |
| A | 0 d | 41.12 ± 3.96 | | 8.48 ± 2.17 | |
| | 17 d | 44.43 ± 4.03 | 8.05 | 7.93 ± 1.90 | −6.49 |
| | 27 d | 45.04 ± 3.30* | 9.51 | 7.34 ± 1.73 | −13.44 |
| B | 0 d | 38.66 ± 3.90 | | 9.16 ± 4.02 | |
| | 17 d | 43.54 ± 3.32** | 12.62 | 8.26 ± 2.90* | −9.83 |
| | 27 d | 46.34 ± 3.48** | 19.87 | 7.26 ± 2.07** | −20.74 |
| C | 0 d | 40.72 ± 3.65 | | 8.64 ± 5.43 | |
| | 17 d | 46.94 ± 3.54** | 15.28 | 7.51 ± 1.99** | 13.08 |
| | 27 d | 49.14 ± 3.03** | 20.68 | 7.04 ± 1.97** | −18.52 |
| D | 10 d | 38.72 ± 3.08 | | 9.27 ± 5.07 | |
| | 17 d | 42.87 ± 3.32 | 10.72 | 8.22 ± 2.96 | −11.33 |
| | 27 d | 47.16 ± 3.90 | 21.80 | 7.33 ± 1.85 | −20.93 |

Measurement of skin moisture: using a corneometer; performing the nondestructive testing on the skin through a volumetric sensor; and obtaining a value of the moisture content of the skin; and counting the change degrees of percentage before and after applying the skin care products, namely, a moisture change rate=(a detected value−a base value)/the base value.

Measurement of water loss: using a tewameter; directly measuring the content of moisture evaporated from epidermis by performing the nondestructive testing on the skin; and counting the change degrees of percentage before and after applying the skin care products, namely, the change rate of moisture loss=(the detected value−the base value)/the base value.

The above table shows that after 10 female volunteers continuously use the Borojo skin care products of the present invention for 17 days, the skin has good compatibility of products, no significant skin irritation, allergy and other adverse reactions are observed, the conditions of moisture content and moisture loss of the skin have significant difference in comparison with the skin before use; after continuing to use the Borojo skin care products of the present invention for 30 days, the increase of the moisture content of the skin and the decrease of the moisture loss of the skin are improved significantly, and the skin moisturizing/nourishing effect is enhanced significantly in comparison to that when the skin care product is used for 17 days.

Finally, it should be noted that the above embodiments are only used for describing the technical solution of the present invention, rather than limiting the protection scope of the present invention; although the present invention is described in detail by reference to the preferred embodiments, those skilled in the art should understand that they can modify or equivalently replace the technical solution of the present invention, without departing from the essence and scope of the technical solution of the present invention.

We claim:

1. A topical Borojo skin care product, consisting essentially of a cosmetic matrix and an enzymatic Borojo powder; wherein the mass concentration of the enzymatic Borojo powder in the skin care product is 0.1-5%; and
   wherein the enzymatic Borojo powder is prepared by a method comprising the following steps:
   a: taking fresh Borojo fruits, cleaning and peeling, and separating kernels from the fruits;
   b: adding water of 10% by weight of fruit flesh to the fruit flesh, grinding, then adding pectinase of 1% by weight of fruit flesh, conducting enzymatic digestion on the fruit flesh for 1.5 hours at 30-40° C.;
   c: pressing and filtering the fruit flesh after enzymatic digestion and removing impurities, heating to 80° C. and keeping the temperature for 5 min;
   d: adding sodium carbonate of 5% by weight of fruit flesh to adjust the pH, and then concentrating in vacuum at −65° C. until the BRIX reaches 20%; and
   e: adding beta-cyclodextrin of 1% by weight of the fruit flesh, and then spraying-drying to obtain the Borojo powder.

2. A preparation method for the Borojo skin care product according to claim 1, wherein the method comprises the steps of mixing and uniformly stirring the Borojo powder in the matrix to obtain the product.

3. The Borojo skin care product of claim 1, wherein the mass concentration of the Borojo powder in the skin care product is 5%.

* * * * *